US012797181B2

(12) United States Patent
Dacosta et al.

(10) Patent No.: US 12,797,181 B2
(45) Date of Patent: Nov. 17, 2026

(54) SOFT TISSUE IMPLANTS, INSTRUMENTATION, AND METHODS

(71) Applicant: Paragon 28, Inc., Englewood, CO (US)

(72) Inventors: Albert Dacosta, Lone Tree, CO (US); Benjamin Majors, Englewood, CO (US); Paul Devasconcellos, Parker, CO (US); Kyle James Hartson, Denver, CO (US); Randy Allard, Golden, CO (US)

(73) Assignee: Paragon 28, Inc., Englewood, CO (US)

(*) Notice: Subject to any disclaimer, the term of this patent is extended or adjusted under 35 U.S.C. 154(b) by 275 days.

(21) Appl. No.: 18/624,086

(22) Filed: Apr. 1, 2024

(65) Prior Publication Data

US 2025/0302607 A1 Oct. 2, 2025

(51) Int. Cl.
*A61F 2/08* (2006.01)
*A61B 17/04* (2006.01)

(52) U.S. Cl.
CPC ..... *A61F 2/0811* (2013.01); *A61B 2017/0464* (2013.01); *A61B 2017/0496* (2013.01)

(58) Field of Classification Search
CPC ........ A61B 17/0401; A61B 2017/0409; A61B 2017/0414; A61B 2017/044; A61B 2017/0445; A61B 2017/0464; A61B 2017/0496; A61F 2/0811
USPC .......................................................... 606/232
See application file for complete search history.

(56) References Cited

U.S. PATENT DOCUMENTS

| | | | |
|---|---|---|---|
| 6,045,573 A * | 4/2000 | Wenstrom, Jr. | A61B 17/0401 606/232 |
| 10,441,450 B2 | 10/2019 | Saadat et al. | |
| 2006/0247641 A1 | 11/2006 | Re | |
| 2008/0033460 A1 | 2/2008 | Ziniti et al. | |
| 2009/0118776 A1 | 5/2009 | Kelsch | |

(Continued)

FOREIGN PATENT DOCUMENTS

WO 2013114347 8/2013

OTHER PUBLICATIONS

International Search Report and Written Opinion of the International Searching Authority for PCT/US2022/013302, Jun. 8, 2022, 10 pages.

(Continued)

*Primary Examiner* — Jocelin C Tanner
(74) *Attorney, Agent, or Firm* — Heslin Rothenberg Farley & Mesiti P.C.

(57) ABSTRACT

A system for repairing or reconstructing soft tissue includes an instrument having a handle and an extension, the extension opposite the handle, an implant releasably engaged with the instrument, and a suture threaded through at least a portion of the implant, wherein the suture is engaged with a tensioning mechanism of the instrument. The implant includes a top portion, a bottom portion and a body portion that is disposed between the top portion and the bottom portion. The top portion, the bottom portion, and the body portion are arranged about a common longitudinal axis and is monolithic. The implant is cannulated through the top portion and at least a portion of at least either the body portion and/or the bottom portion. The implant also may include at least one vent disposed along an outer surface of either or both the top portion and the body portion.

20 Claims, 37 Drawing Sheets

(56) References Cited

U.S. PATENT DOCUMENTS

| | | | | |
|---|---|---|---|---|
| 2014/0052177 | A1 | 2/2014 | Singhatat | |
| 2015/0142052 | A1 | 5/2015 | Koogle, Jr. et al. | |
| 2017/0135688 | A1 | 5/2017 | Branthover et al. | |
| 2019/0167252 | A1 | 6/2019 | Nason et al. | |
| 2019/0336190 | A1 | 11/2019 | Allard et al. | |
| 2019/0336270 | A1 | 11/2019 | DaCosta et al. | |
| 2020/0022693 | A1 | 1/2020 | Lantz et al. | |
| 2020/0155140 | A1 | 5/2020 | Palese | |
| 2021/0000588 | A1 * | 1/2021 | Cain ..................... | A61F 2/0811 |
| 2023/0355231 | A1 | 11/2023 | Dacosta | |

OTHER PUBLICATIONS

International Preliminary Report on Patentability for International Application No. PCT/US2022/013302 dated Jul. 20, 2023, 7 pages, International Bureau of WIPO.
International Search Report and Written Opinion in International Application No. PCT/US2025/022384, mailed by the United States Patent Office on Jun. 16, 2025, 9 pages.
European Patent Office, Supplementarty Partial European | Search Report for European Application No. 22743243.2 dated Oct. 21, 2024, 14 pages.

* cited by examiner

SOFT TISSUE IMPLANTS, INSTRUMENTATION, AND METHODS

TECHNICAL FIELD

The present disclosure relates to soft tissue implant systems, instruments, and related methods. The present disclosure relates to podiatric and orthopedic implants and surgery related to repairs of soft tissue and/or bone. More specifically, but not exclusively, the present disclosure relates to instruments, implants, devices, systems, assemblies, and methods for joining soft tissue to soft tissue, soft tissue to bone, and bone to bone.

BACKGROUND OF THE INVENTION

Many currently available implants, instrumentation, systems, and methods for addressing soft tissue trauma (acute and chronic, e.g., defect, gradual deterioration, etc.) do not completely address the needs of patients. Additionally, many currently available implants, instrumentation, systems, and methods for addressing soft tissue trauma fail to account for properties of soft tissue anatomy and further require healthcare providers to perform steps that can reduce the efficiency of the procedure as well as the favorability of the outcome for the patient.

SUMMARY OF THE INVENTION

The present disclosure is directed toward soft tissue implants, implant systems, instruments, and related methods.

A first aspect of the present disclosure is a system for repairing or reconstructing soft tissue. The system includes an instrument having a handle and an extension, the extension opposite the handle, an implant releasably engaged with the instrument, and a suture threaded through at least a portion of the implant, wherein the suture is engaged with a tensioning mechanism of the instrument.

According to the first aspect of the present disclosure, the implant includes a top portion, a bottom portion, and a body portion disposed between the top portion and the bottom portion, wherein the top portion, the bottom portion, and the body portion are arranged about a common longitudinal axis.

According to the first aspect of the present disclosure, the implant is cannulated through the top portion and at least a portion of at least one of the body portion and the bottom portion.

According to the first aspect of the present disclosure, the implant includes least one vent disposed along an outer surface of at least one of the top portion and the body portion, wherein the at least one vent establishes fluid communication between the outer surface and an inner surface the implant.

According to the first aspect of the present disclosure, the implant includes a threading disposed along at least a portion of the outer surface of the top portion and the body portion, wherein the threading includes a plurality of threads equidistantly spaced from one another.

According to the first aspect of the present disclosure, the threading is configured to span at least a portion of the at least one vent.

According to the first aspect of the present disclosure, the implant includes at least one tap arranged on an outer surface of the bottom portion of the implant.

According to the first aspect of the present disclosure, the at least one tap includes a plurality of taps arranged about the outer surface of the bottom portion of the implant, wherein the plurality of taps protrude from the outer surface and are equidistantly spaced from one another.

According to the first aspect of the present disclosure, the implant is releasably couplable with a tip of the extension of the implant.

According to the first aspect of the present disclosure, the instrument comprises a tensioning mechanism disposed within a housing of the instrument.

According to the first aspect of the present disclosure, the tensioning mechanism includes a first arm, a second arm, and a resilient member.

According to the first aspect of the present disclosure, the second arm is pivotably coupled with the first arm.

According to the first aspect of the present disclosure, the instrument includes a track disposed on at least a portion of the outer surface of the handle, wherein the track is configured to receive at least a portion of a suture at least partially therein.

According to the first aspect of the present disclosure, the second arm includes an engagement portion configured to engage with at least a portion of the suture, wherein the engagement portion is arranged adjacent to at least a portion of the track.

According to the first aspect of the present disclosure, the resilient member is a spring.

According to the first aspect of the present disclosure, actuation of at least one of the first arm and the second arm compresses the spring.

A second aspect of the present disclosure includes an instrument. The instrument includes a handle having a housing. The housing includes a tensioning mechanism having a first arm, a second arm pivotably coupled with the first arm, and a resilient member. The handle also includes a track disposed on at least a portion of an outer surface of the housing, wherein the track is configured to receive at least a portion of a suture. The instrument also includes an extension configured to releasably couple with an implant.

According to the second aspect of the present disclosure, the second arm includes an engagement portion configured to releasably engage with at least a portion of the suture such that actuation of the second arm engages and disengages the engagement portion with at least a portion of the suture.

A third aspect of the present disclosure includes an implant. The implant includes an upper portion with at least one vent disposed in an outer surface of the upper portion and establishing fluid communication between the outer surface and an inner surface of the upper portion. The implant also includes a threading disposed on the outer surface of the upper portion, wherein the threading is configured to span the at least one vent. The implant also includes an bottom portion, with the upper portion and the bottom portion having a substantially cylindrical geometry and are arranged concentrically about a common longitudinal axis.

According to the third aspect of the present disclosure, at least the upper portion of the implant is cannulated.

BRIEF DESCRIPTION OF THE DRAWINGS

The accompanying drawings, which are incorporated in and constitute a part of the specification, illustrate embodiments of the inventions and together with the detailed description herein, serve to explain the principles of the inventions. It is emphasized that, in accordance with the standard practice in the industry, various features may or may not be drawn to scale. In fact, the dimensions of the various features may be arbitrarily increased or reduced for clarity of discussion. The drawings are only for purposes of illustrating embodiments of inventions of the disclosure and are not to be construed as limiting the inventions.

DETAILED DESCRIPTION OF THE INVENTION

Figure 1:
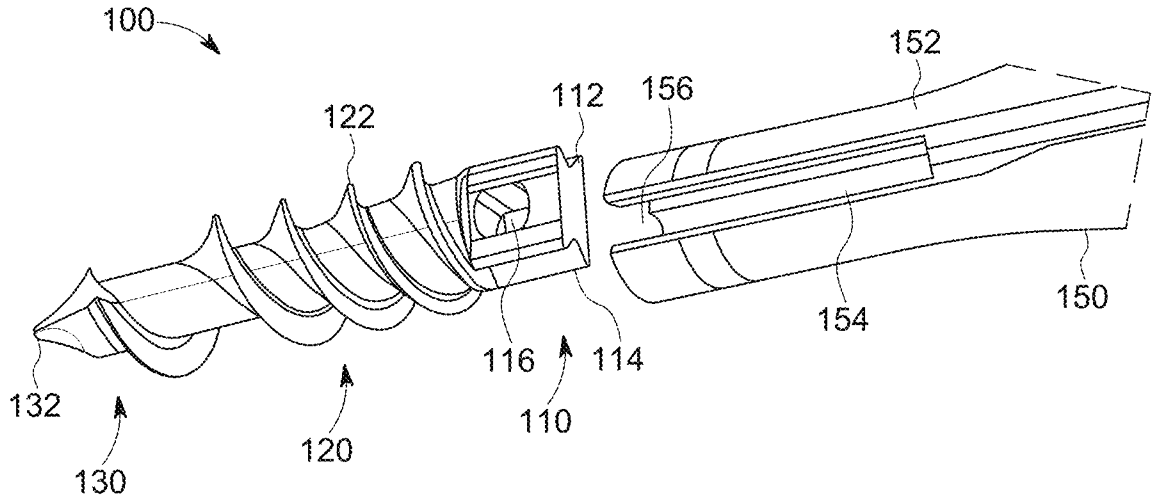
FIG. 1 is a side perspective view of an exemplary implant and instrument for facilitating soft tissue repair and/or reconstruction in conjunction with an implant system, in accordance with the present disclosure.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current implants, devices, instrumentation, and methods are described herein with reference to use with the bones of the foot, the bones of the foot, ankle and lower leg may be used to describe the surfaces, positions, directions or orientations of the implants, devices, instrumentation and methods. Further, the implants, devices, instrumentation, and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, instrumentation, and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, instrumentation, and methods, and the aspects, components, features and the like thereof, described herein with respect to the right foot may be mirrored so that they likewise function with the left foot. Further, the implants, devices, instrumentation, and methods, and the aspects, components, features and the like thereof, disclosed herein are described with respect to the foot for brevity purposes, but it should be understood that the implants, devices, instrumentation, and methods may be used with other bones of the body having similar structures.

The instruments, implants, systems, assemblies, and related methods for repairing, reconstructing, or facilitating the repair/reconstruction of the present disclosure may be similar to, such as include at least one feature or aspect of, the implants, systems, assemblies and related methods disclosed in International PCT Application No. PCT/US2020/070866, filed on Dec. 4, 2020, and entitled Soft Tissue Repair; U.S. Provisional Application No. 62/968,965, filed Jan. 31, 2020, and entitled Knotless Soft Tissue Implant Systems and Related Methods; and/or U.S. Provisional Application No. 63/034,066 filed on Jun. 3, 2020, entitled Soft Tissue Implant Systems, Instruments, and Related Methods; which are hereby incorporated herein by reference in their entireties. Similarly, the instruments, implants, systems, assemblies, and related methods for maintaining, correcting, and/or resurfacing joint surfaces of the present disclosure may include one or more instrument (e.g., one or more insertion and/or implantation instruments) disclosed in International PCT Application No. PCT/US2020/070866, filed on Dec. 4, 2020, and entitled Soft Tissue Repair; U.S. Provisional Application No. 62/968,965, filed Jan. 31, 2020, and entitled Knotless Soft Tissue Implant Systems and Related Methods; and/or U.S. Provisional Application No. 63/034,066 filed on Jun. 3, 2020, entitled Soft Tissue Implant Systems, Instruments, and Related Methods; which are hereby incorporated herein by reference in their entireties.

Referring to the drawings, wherein like reference numerals are used to indicate like or analogous components throughout the several views, and with particular reference to FIG. 1, there is illustrated an exemplary embodiment of an implant 100 (e.g., anchor, etc.) for fixation within bone and/or soft tissue so as to facilitate repair and/or reconstruction of soft tissue. Also shown in FIG. 1 is an instrument 150 configured to engage with and/or facilitation the implantation, manipulation, adjustment, and/or removal of the implant 100. The implant 100 is shown to include a top portion 110 and a bottom portion 130, with a body portion 120 disposed between the top portion 110 and the bottom portion 130. The top portion 120 of the implant 100 is shown to include a head 112 arranged at the proximal end of the top portion of the implant 100. As shown in the exemplary embodiment of FIG. 1, the head 112 includes an interface feature 114 positioned at the proximal end of the top portion 110. The interface feature 114 is configured to engage (e.g., interface, releasably couple with, receive a portion of, etc.) with at least a portion of the instrument 150. The instrument 150 is shown to include an interface feature 154 arranged on a distal portion 152 of the instrument 150, with the interface feature 154 having a complimentary geometry to that of the interface feature 114 of the implant 100. Further, the instrument 150 is shown to include a recess 156 arranged on the distal portion 152 of the instrument 150. The recess 156 is shown to include at least a portion of the substantially cylindrical geometry of the distal portion 152 and may be configured to align with one or more portions of the implant 100 to facilitate threading of one or more needles and/or sutures. As shown in the exemplary embodiment, of FIG. 1, the interface feature 114 is shown to have a hexalobe geometry. In alternate embodiments, the interface feature 114 may have alternate geometries, for example a traditional torx geometry, a hexagonal geometry or various geometries with one or more splines arranged variously about the interface feature 114. Accordingly, such alternate geometries of the interface feature 114 may be configured to accommodate a portion of one or more instruments as mentioned previously, for example a driver or other instrument.

The top portion 110 is further shown to include an opening (e.g., an aperture, eyelet, etc.) 116 configured to receive a suture threaded through said opening 116. As shown in the exemplary embodiment of FIG. 1, the opening 116 is defined in lateral directions by at least a portion of the interface feature 114, and in a distal direction by at least a portion of the body portion 120. The opening 116 may be arranged such that when the implant 114 interfaces with an instrument 150 such as those previously mentioned, the opening 116 is aligned with and/or positioned adjacent one or more openings of said instruments (e.g., the recess 156 of the instrument 150). For example, the instrument 150 may include a shaft with diametrically opposed openings with which the opening 116 may align when the implant 100 engages with the instrument 150 via at least the interface feature 114. The alignment of the openings of the instrument 150 with the opening 116 of the implant 100 may be configured to facilitate threading of a suture through one opening of the instrument 150, through the opening 116 of the implant 100 engaged with the instrument 150, and subsequently through a second opening of the instrument 150. Such threading of a suture through the opening 116 engages the suture with the implant 100 prior to implantation and further allows for the implant 100 to be implanted within bone and/or soft tissue without requiring an intermediate step to thread the suture after implantation has been initiated. Following implantation, the instrument 150 may be disengaged from the interface feature 114 of the implant 100 and the suture, with the suture then free to be secured and/or manipulated as needed (e.g., coupled with one or more other implants, tensioned, etc.).

The body portion 120 of the implant 100 is shown to include a threading 122 arranged along a length of the body portion 120. In some embodiments, the threading 122 may extend proximally along the body portion 120 such that the threading 122 terminates adjacent and/or abuts the interface feature 114 of the top portion 110. Further, the threading 122 may further extend distally such that the threading 122 terminates at a distal portion of the bottom portion 130 of the implant 100. The threading 122 is shown to extend circumferentially around the implant 100 while extending continuously from the bottom portion 130 to the top portion 110. As shown in the exemplary embodiment of FIG. 1, the threading 122 is a dual-lead thread while in alternate embodiments, the threading 122 may be a single-lead threading. In some embodiments, the threading 122 may include alternate configurations and/or lengths. The threading 122 is shown to include substantially equivalent spacing (e.g., distance between the threads in the proximal-distal direction when viewed from a side view such as that shown in FIG. 1) along the body portion 120 of the implant 100, with the threading 122 having a greater spacing on the bottom portion 130 of the implant 100. In some embodiments, the threading 122 may have equivalent spacing along the length of the implant 100, whereas in other embodiments the threading 122 may have one or more different spacing intervals along the length of the implant 100. The threading 122 may terminate in a tip portion 132 of the bottom portion 130 as shown in the exemplary embodiment of FIG. 1. The tip portion 132 may be configured to facilitate implantation of the implant 100 into bone and/or soft tissue. Further, as the implant 100 is implanted in bone and/or soft tissue, soft tissue may be pulled in the direction in which the implant 100 is being inserted (e.g., into the bone) so as to achieve the desired placement of soft tissue from a displaced position. Once the implant 100 is implanted, the implant 100 may be disengaged from any instrument implemented during the implantation procedure of the implant 100 and the suture may be tied off and/or coupled with other adjacent implants, anatomy, or sutures.

The implant 100 may have one or more standard lengths, with the length measured from the proximal-most point of the top portion 110 to the distal-most portion of the bottom portion 130. For example, the implant 100 may have a length ranging from 2 mm to 6 mm, with various different sized produced and/or provided in a surgical kit in increments of 0.5 mm. Additionally, the embodiment of the implant 100 shown in FIG. 1 may be available in multiple lengths (e.g., as components of a surgical kit or independently) so as to accommodate different applications of implantation into bone and/or soft tissue to facilitate repair and/or reconstruction of the soft tissue. Further, the implant 100 may have a standard diameter and/or may be available in various different diameters so as to accommodate different applications of implantation into bone and/or soft tissue to facilitate repair and/or reconstruction of the soft tissue. Such various diameters may be components of a surgical kit (e.g., a sterile kit including multiple lengths and diameters of the implant 100 as well as other components, for example one or more k-wires, drills, and/or drivers) and/or may be available independently of such a kit. The implant 100 may preferably be fabricated from titanium, although the implant 100 may also be available in PEEK and/or other polymeric soft anchor configurations. In some aspects, the implant 100 may be produced and/or provided with a suture (e.g., those shown and described in the patent applications referenced previously, or other similar sutures and/or suture tapes) threaded through the opening 116. Further, in some aspects the implant 100 may be produced and/or provided (e.g., in a sterile surgical kit) in a pre-loaded state, where the implant 100 is engaged with an instrument 150 via the interface feature 114 and a suture as described previously threaded through the implant 100 and at least a portion of the instrument 150.

Figure 2:
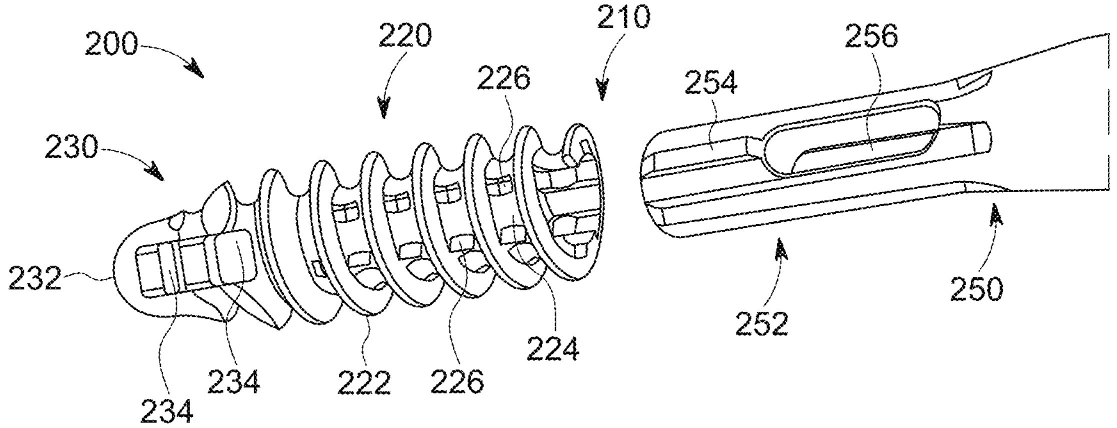
FIG. 2 is a side perspective view of an exemplary implant and instrument for facilitating soft tissue repair and/or reconstruction in conjunction with an implant system, in accordance with the present disclosure.
Figure 3:
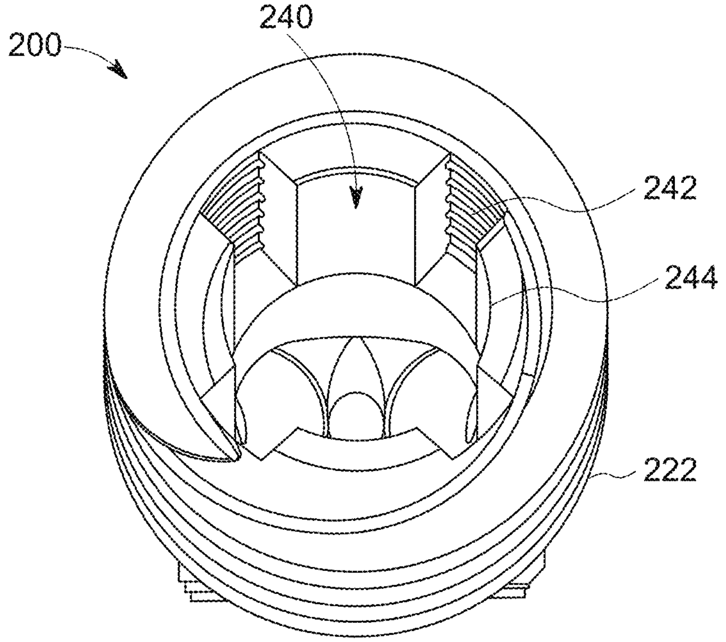
FIG. 3 is a top end perspective view of the implant of FIG. 2 for facilitating soft tissue repair and/or reconstruction in conjunction with an implant system, in accordance with the present disclosure.
Figure 4:
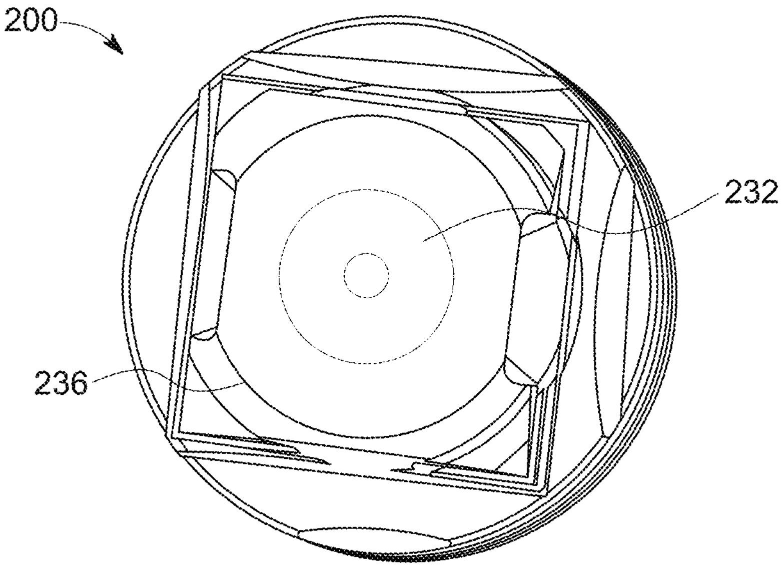
FIG. 4 is bottom end perspective view of the exemplary implant of FIG. 2 facilitating soft tissue repair and/or reconstruction in conjunction with an implant system, in accordance with the present disclosure.

Referring now to FIGS. 2-4, an exemplary embodiment of an implant 200 is shown. The implant 200 is shown to include a top portion 210, a bottom portion 230, and a body portion 220 arranged between the top portion 210 and the bottom portion 230. The implant 200 is further shown to include a channel (e.g., a cannulated opening) 240 extending along a longitudinal axis of the implant 200 from the proximal-most point of the top portion 210 through the body portion 220 and terminating at the distal-most point of the body portion 220. The implant 200 is shown to include an interface feature 242 arranged within the channel 240 and, as shown in the exemplary embodiment of FIGS. 2-4, disposed circumferentially about an inner surface 244 of the implant 200. The interface feature 242 of exemplary embodiment of the implant 200 shown in FIGS. 2-4 includes four splines arranged circumferentially about the inner surface 244 of the implant 200 and extending along the inner surface 244 from the top portion 210 of the implant 200 in a distal direction, with each of the splines positioned in approximately 90-degree increments (e.g., the splines are equally spaced circumferentially about the inner surface 244). In some embodiments, the interface feature 242 may include a greater or lesser number of splines, for example one, two, three, five, or another alternate number of splines. Further, the splines of the interface feature 244 may be arranged variously about the inner surface 244 of the implant 200, for example in some embodiments the splines may not have approximately equal spacing from one another as shown and described in FIG. 3. In some embodiments, the splines may include a geometry other than that shown and described with reference to FIG. 3, for example the splines may include a substantially triangular geometry.

The interface feature 242 is configured to engage (e.g., receive, releasably couple with, etc.) one or more instruments that may be provided in a surgical kit along with the implant 200. As shown in FIG. 2, an instrument (e.g., a driver) 250 is shown to include an interface feature 254 arranged on a distal portion 252 of the instrument 250. The interface feature 254 of the instrument 250 is shown to be complimentary (e.g., geometrically opposite) to that of the interface feature 242. As shown in FIG. 2, the interface feature 254 of the instrument 250 includes four splines complimentary to those of the interface feature 242 of the implant 200. In some embodiments, the complimentary four splines of the interface features 242, 254 may be configured to accommodate greater torque than other similar geometries (e.g., torque from the instrument 250 being applied to the implant 200 so as to implant the implant 200 in bone and/or soft tissue). The distal portion 252 of the instrument 250 may be received (e.g., to engage, releasably couple, etc.) within the channel 240 of the implant 200 such that the interface feature 254 engages with the interface feature 242 along at least a portion of the length of the interior surface 244 of the channel 240. The instrument 250 is further shown to include an opening 256 arranged on the distal portion 252 thereof, with the opening 256 configured such that it may align with one or more components of the implant 200 (e.g., slots, openings, vents, engagement features, etc.). In some embodiments, the implant 200 may be produced and/or provided (e.g., as part of a sterile surgical kit) with the implant 200 in an engaged position such that the interface feature 242 of the implant 200 is engaged with the interface feature 254 of the instrument 200. In some embodiments, the interface feature 254 of the instrument 250 may include alternate geometries, for example an alternate number of splines equivalent to that of the interface feature 254 of the instrument 250. Further, in some embodiments the interface features 242, 254 may include alternate complimentary geometries (e.g., torx, hexagonal, etc.).

The implant 200 includes a threading 222 arranged on an outer surface 224 of the implant 200 and extending from a proximal-most portion of the top portion 210 to the bottom portion 230 of the implant 200. As shown in FIGS. 2-4, the threading 222 is equally spaced (e.g., an equal spacing between threads when viewed from a side direction) along the length of the outer surface 224 of the implant 200. As shown in FIGS. 2-4, the threading 222 is a four-lobed thread, although the threading 222 may have other configurations in alternate embodiments. The implant 200 is further shown to include a plurality of vents (e.g., openings) 226 positioned on the outer surface 224 of the implant 200. As shown in the exemplary embodiment of FIG. 2, the vents 226 extend from the proximal-most portion of the top portion 210 to the distal-most portion of the body 220. The implant 200 as shown includes four vents arranged circumferentially about the outer surface 224 of the implant 200 and substantially equidistant from one another (e.g., at approximately 90-degree increments). The vents 226 are shown to extend from the outer surface 224 of the implant 200 to the inner surface 244 of the implant 200, thus establishing fluid communication between the outer surface 244 of the implant 200 and the channel 240. It should be noted that the vents 226 are arranged so as not to interfere with the interface feature 242 and that the interior surface 244 of the implant 200 may include alternating vents 226 and splines of the interface feature 242 arranged circumferentially within the channel 240. Further, the vents 226 may be configured to align with the openings 256 of the instrument 250 when in an engaged position. After implantation, the vents 226 are configured to facilitate bone ingrowth thus providing additional fixation within the bone and/or soft tissue. In some embodiments, the implant 200 may have greater or fewer than the four vents 226 shown in FIG. 2, where the vents 226 may be arranged alternately (e.g., not equidistant circumferentially from one another) about the outer surface 224 of the implant 200. The threading 222 is shown to extend around the body portion 220 from the bottom portion 230 to the top portion 210, with the threading 222 traversing the vents 226 as shown in FIG. 2.

The bottom portion 230 of the implant 200 is shown to include openings 234 extending laterally (e.g., substantially diametrically) through the bottom portion 230 of the implant 200. As shown in FIG. 2, the channel 240 terminates proximal relative to the openings 234 in the bottom portion 230 of the implant 200 such that the openings 234 are at least partially defined in the longitudinal direction by an interior portion 236 of the bottom portion 230 of the implant 200. The openings 234 are configured to receive one or more sutures which may be threaded prior to implantation, and furthermore may be threaded prior to engagement of the implant 200 with the instrument 250 (e.g., a surgical kit may include the implant 200 engaged with the instrument 250 with one or more sutures threaded through the openings 234). In some embodiments, the implant 200 may include a single opening 234 or may include three or more openings 234 arranged variously about the bottom portion 230 of the implant 200.

The implant 200 includes a tip 232 arranged at the distal-most portion of the bottom portion 230. As shown in FIG. 2, the tip 232 is substantially rounded but may have alternate geometries in other embodiments. The tip 232 is shown to include a tap feature 236 shown for example as a square tap in the exemplary embodiment of FIGS. 2-4. The tap feature 236 (see FIG. 4) is configured to facilitate implantation in the bone and/or soft tissue (including, for example, especially dense bone) without requiring additional instruments or tools (e.g., a drill to create a pilot hole, etc.). Accordingly, a physician may insert the implant 200 via the tap feature 236 into the bone in a time-efficient and instrument-efficient manner (which does not require obtaining and switching between multiple instruments). In some embodiments, the tap feature 236 may include geometries other than the square geometry shown and described with reference to FIG. 4. Further, in some embodiments (and depending on the material of which the implant 200 consists of), the tip 232 adjacent the tap feature 236 may include cutting flutes configured to facilitate implantation (for example, a metal embodiment may include cutting flutes, whereas a PEEK embodiment may include a square tap feature 236 as shown).

The implant 200 may have one or more standard lengths, with the length measured from the proximal-most point of the top portion 210 to the distal-most portion of the bottom portion 230. For example, the implant 200 may have a length ranging from 2 mm to 6 mm, with various different sizes produced and/or provided in a surgical kit in increments of 0.5 mm. Additionally, the embodiment of the implant 200 shown in FIGS. 2-4 may be available in multiple lengths (e.g., as components of a surgical kit or independently) so as to accommodate different applications of implantation into the bone and/or soft tissue to facilitate repair and/or reconstruction of the soft tissue. Further, the implant 200 may have a standard diameter and/or may be available in various different diameters so as to accommodate different applications of implantation into the bone and/or soft tissue to facilitate repair and/or reconstruction of the soft tissue. Such various diameters may be components of a surgical kit (e.g., a sterile kit including multiple lengths and diameters of the implant 200 as well as other components, for example one or more k-wires, drills, and/or drivers) and/or may be available independently of such a kit. The implant 200 may be fabricated from metal (e.g., titanium), or one or more forms of PEEK (e.g., HA Peek, carbon fiber reinforced PEEK, HA/CF PEEK, natural PEEK, etc.) and/or other polymeric material. In some aspects, the implant 200 may be produced and/or provided with a suture (e.g., those shown and described in the patent applications referenced herein previously, or other similar sutures and/or suture tapes) threaded through the openings 234. Further, in some aspects the implant 200 may be produced and/or provided (e.g., in a sterile surgical kit) in a pre-loaded state, where the implant 200 is engaged with the instrument 250 via the interface features 244, 250 and a suture as described previously threaded through the implant 200.

Figure 5:
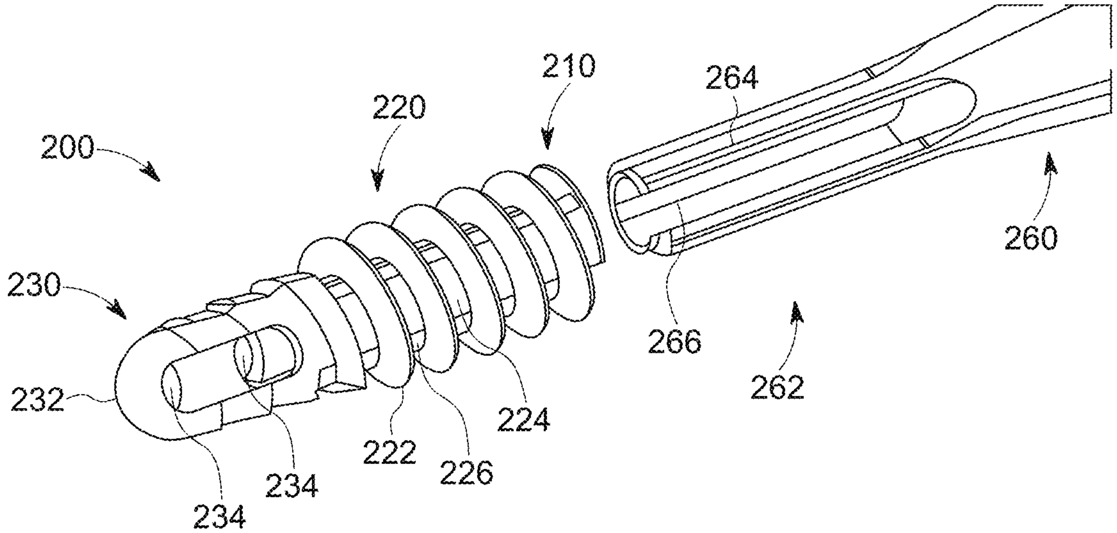
FIG. 5 is a side perspective view of the exemplary implant of FIG. 2 and an additional instrument for facilitating soft tissue repair and/or reconstruction in conjunction with an implant system, in accordance with the present disclosure.

Referring now to FIG. 5, the implant 200 is shown with an instrument 260 for facilitating implantation, manipulation, adjustment, and/or removal of the implant 200. The instrument 260 may have one or more components/features the same as or similar to the instrument 250 as shown and described previously. Further, the instrument 260 is shown to include an interface feature 264 arranged at a distal portion 262 of the instrument 260. The interface feature 264 may have a geometry that is the same as or similar to that of the interface feature 254, as both interface features 254, 264 are configured to engage with the interface feature 242 of the implant 200. The instrument 260 is further shown to include a recess 266, where the recess 266 includes at least a portion of the cylindrical geometry of the distal portion 262 of the instrument 260. The recess 266 may be configured to facilitate the threading and/or placement of one or more sutures (such as those mentioned previously) and/or needles within/through the recess 266 and/or through one or more elements of the implant 200.

Figure 6:
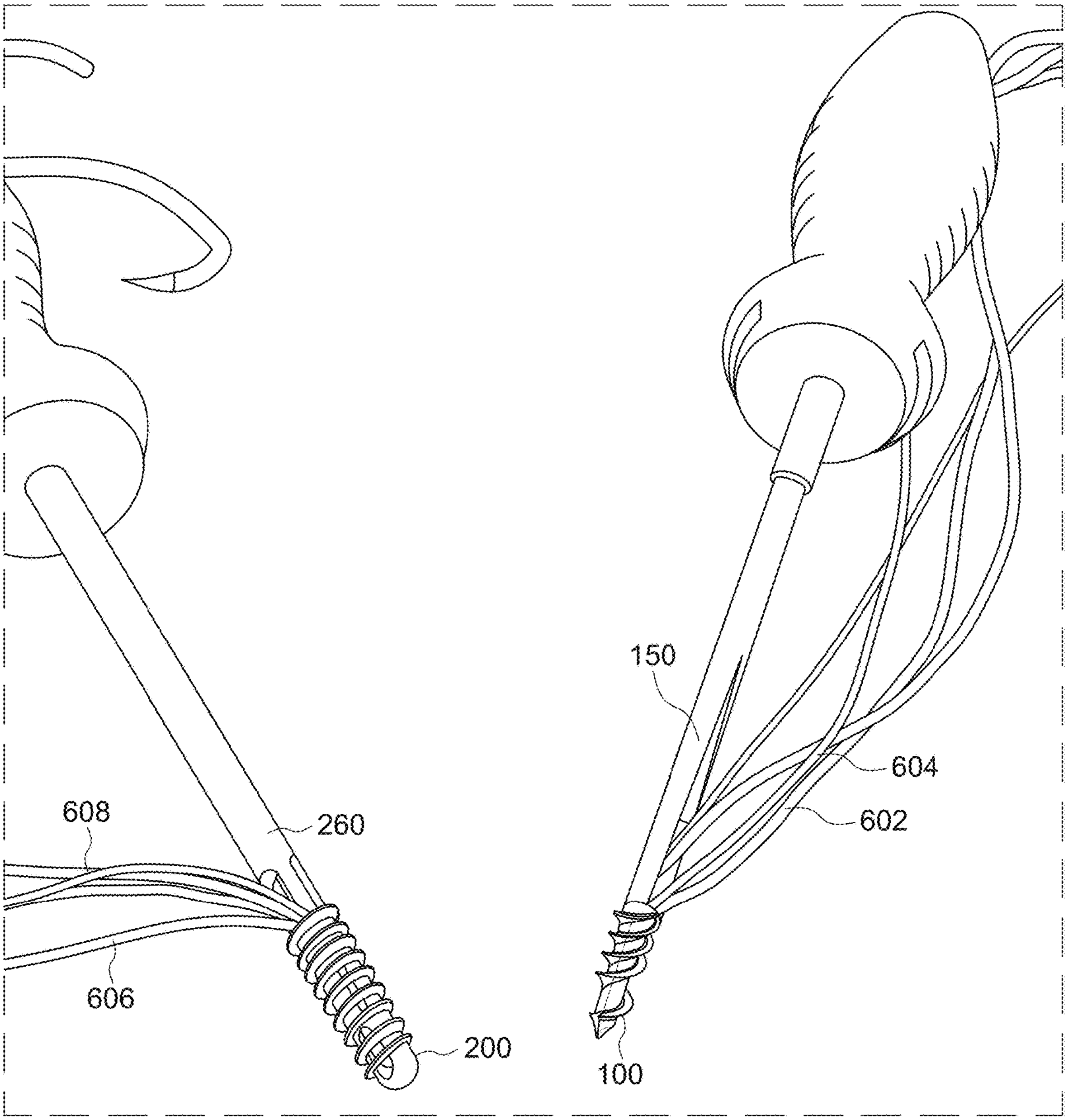
FIG. 6 is a perspective view of the implants and instruments of FIG. 1 and FIG. 5, in accordance with the present disclosure.

Referring now to FIG. 6, the implant 100 and instrument 150 are shown adjacent to the implant 200 and the instrument 260. As shown, the implant 100 is engaged with the instrument 150 via the interface features 114 and 154. Further, a first suture 602 and a second suture 604 are shown to be threaded through the implant 100 and the instrument 150 such that the implant 100 and the instrument 150 are, collectively in a loaded state. As shown, the implant 200 is engaged with the instrument 260 via the interface features 242 and 254. Further, a first suture 606 and a second suture 608 are shown to be threaded through the implant 200 and the instrument 260 such that the implant 200 and the instrument 260 are, collectively in a loaded state. In some aspects, the implant 100 and instrument 150 as well as the implant 200 and the instrument 260 may be produced, provided, and/or sold in the loaded state as shown in FIG. 6.

Figure 7:
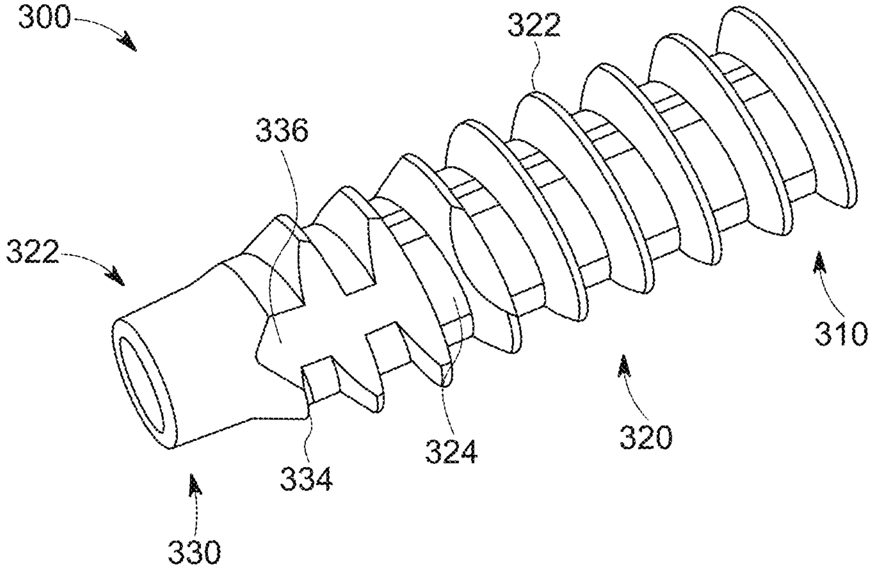
FIG. 7 is a side perspective view of an exemplary implant for facilitating soft tissue repair and/or reconstruction in conjunction with an implant system, in accordance with the present disclosure.
Figure 8:
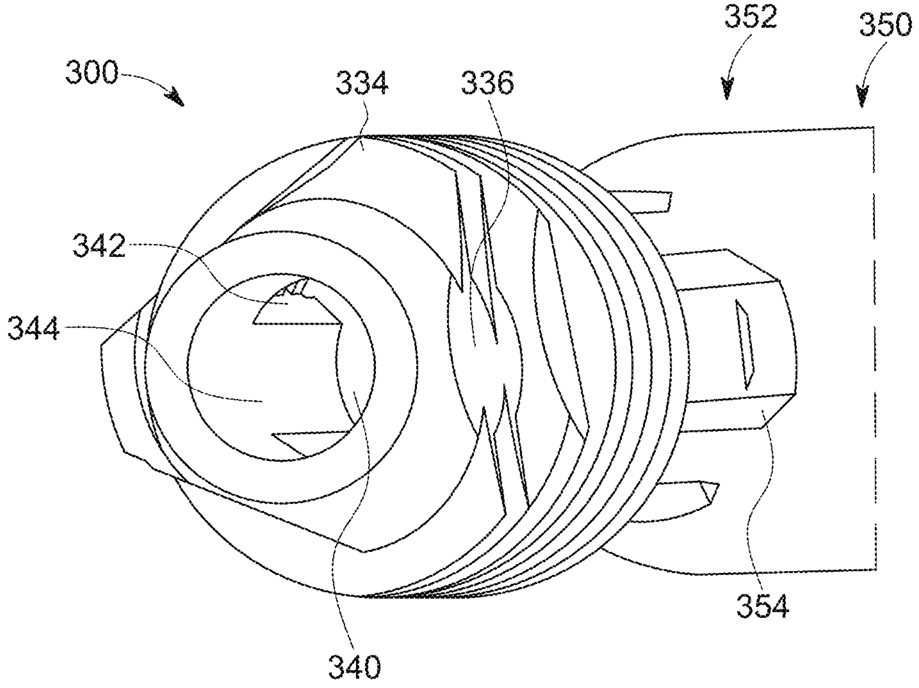
FIG. 8 is bottom end perspective view of the exemplary implant of FIG. 7 for facilitating soft tissue repair and/or reconstruction in conjunction with an implant system, in accordance with the present disclosure.

Referring now to FIGS. 7-8, an implant 300 is shown. The implant 300 includes a top portion 310, a bottom portion 330, and a body portion 320 arranged longitudinally between the top portion 310 and the bottom portion 330. The implant 300 is further shown to include a channel (e.g., a cannulated opening, cannulation, etc.) 340 extending along a longitudinal axis of the implant 300 from the proximal-most point of the top portion 310 through the body portion 320 and extending to and through the distal-most point of the bottom portion 330 thus establishing fluid communication in a longitudinal direction from the top portion 310 to and through the bottom portion 330 of the implant 300. The implant 300 is shown to include an interface feature 342 arranged within the channel 340 and, as shown in the exemplary embodiment of FIGS. 7-8, disposed circumferentially about an inner surface 344 of the implant 300. The interface feature 342 of the exemplary embodiment of the implant 300 shown in FIGS. 7-8 includes four splines arranged circumferentially about the inner surface 344 of the implant 300 and extending along the inner surface 344 from the top portion 310 of the implant 300 in a distal direction, with each of the splines positioned in approximately 90-degree increments (e.g., the splines are equally spaced circumferentially about the inner surface 344). In some embodiments, the interface feature 342 may include a greater or lesser number of splines, for example one, two, three, five, or another alternate number of splines. Further, the splines of the interface feature 344 may be arranged variously about the inner surface 344 of the implant 300, for example in some embodiments the splines may not have approximately equal spacing from one another as shown and described in FIGS. 7-8. In some embodiments, the splines may include a geometry other than that shown and described with reference to FIGS. 7-8, for example the splines may include a substantially triangular geometry.

The interface feature 344 is configured to engage (e.g., receive, releasably couple with, etc.) one or more instruments that may be provided in a surgical kit along with the implant 300. As shown in FIGS. 7-8, an instrument (e.g., a driver) 350 is shown to include an interface feature 354 arranged on a distal portion 352 of the instrument 350. The interface feature 354 of the instrument 350 is shown to be complimentary (e.g., geometrically opposite) to that of the interface feature 342. As shown in FIGS. 7-8, the interface feature 354 of the instrument 350 includes four splines complimentary to those of the interface feature 342 of the implant 300. In some embodiments, the complimentary splines of the interface features 342, 354 may be configured to accommodate greater torque than other similar geometries (e.g., torque from the instrument 350 being applied to the implant 300 so as to implant the implant 300 in bone and/or soft tissue). The distal portion 352 of the implant 350 may be received (e.g., to engage, releasably couple, etc.) within the channel 340 of the implant 300 such that the interface feature 352 engages with the interface feature 342 along at least a portion of the length of the interior surface 344 of the channel 340. In some embodiments, the implant 300 may be produced and/or provided (e.g., as part of a sterile surgical kit) with the implant 300 in an engaged position such that the interface feature 342 of the implant 300 is engaged with the interface feature 354 of the instrument 300. In some embodiments, the interface feature 354 of the instrument 350 may include alternate geometries, for example an alternate number of splines equivalent to that of the interface feature of the instrument. Further, in some embodiments the interface features 342, 354 may include alternate complimentary geometries (e.g., torx, hexagonal, etc.). Additionally, in some embodiments the interface features 342, 354 may be configured to provide a press fit between the instrument 350 and the implant 300. In some embodiments, this press fit may include feedback to the user, such as a haptic and/or audible "click" or other feedback to confirm engagement of the press fit feature. Further, the press fit feature may include one or more impressions or depressions arranged circumferentially around the inner surface 344 of the channel 340, with the complimentary (e.g., geometrically opposite) feature arranged circumferentially about the distal portion 352 of the instrument 350.

The implant 300 includes a threading 322 arranged on an outer surface 324 of the implant 300 and extending from a proximal-most portion of the top portion 310 to the distal-most portion of the body 320 of the implant. As shown in FIGS. 7-8, the threading 322 is equally spaced (e.g., an equal spacing between threads when viewed from a side direction) along at least a portion of the length of the outer surface 324 of the implant 300. As shown in FIGS. 7-8, the threading 322 is a three-lobed thread, although the threading 322 may have other configurations in alternate embodiments. The implant 300 includes a plurality of flats arranged on an outer surface 324 of the implant 300, with the flats 336 positioned at the distal-most portion of the body portion 320 and extending to the distal-most portion of the bottom portion 330. As shown, the implant 300 includes four flats 336, although alternate embodiments may have more or fewer flats 336. The flats 336 are shown to be arranged equidistant from one another about the circumference of the outer surface 324 of the implant 300 but may be arranged alternatively in other embodiments. The implant 300 is further shown to include a tap feature 334 arranged at the proximal-most portion of the bottom portion 330 of the implant 300. As shown in FIGS. 7-8, the tap feature 334 includes a plurality of cutting flutes (e.g., three as shown in FIGS. 7-8, but greater or fewer cutting flutes in alternate embodiments) arranged circumferentially (e.g., in a singular lateral plane) about the outer surface 324 of the implant 300 and substantially equidistant from one another (e.g., approximately 120-degrees from one another). In alternate embodiments, the tap feature 334 may include one or more cutting flutes alternately arranged about the bottom portion 330 of the implant 300. The tap feature 334 is configured to facilitate implantation in a bone and/or soft tissue (including, for example, especially dense bone) without requiring additional instruments or tools (e.g., a drill to create a pilot hole, etc.). Accordingly, a physician may insert the implant 300 via the tap feature 334 into the bone in a time-efficient and instrument-efficient manner (which does not require obtaining and switching between multiple instruments). In some embodiments, the tap feature 334 may include geometries other than the square geometry shown and described with reference to FIGS. 7-8. The bottom portion 330 of the implant 300 is further shown to include a tip 332 arranged at the distal-most portion of the bottom portion 330. The tip 332 is shown to have a substantially cylindrical geometry, with the cylindrical geometry diametrically equal to or lesser than that of the body portion 320 and the top portion 310.

Figure 9:
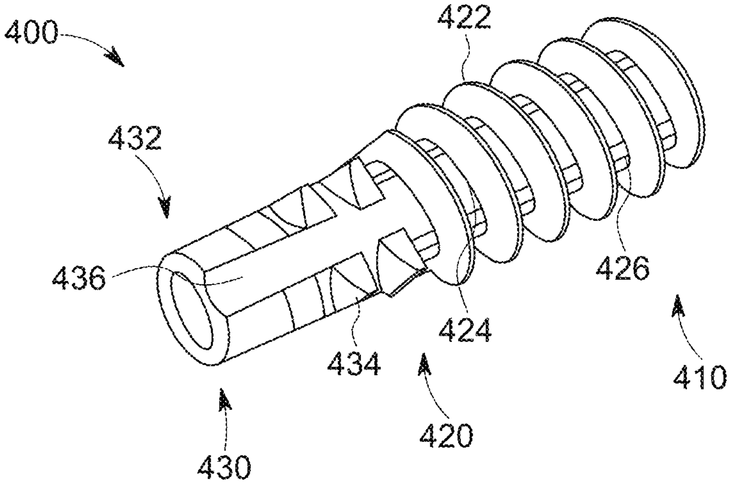
FIG. 9 is a side perspective view of an exemplary implant for facilitating soft tissue repair and/or reconstruction in conjunction with an implant system, in accordance with the present disclosure.
Figure 10:
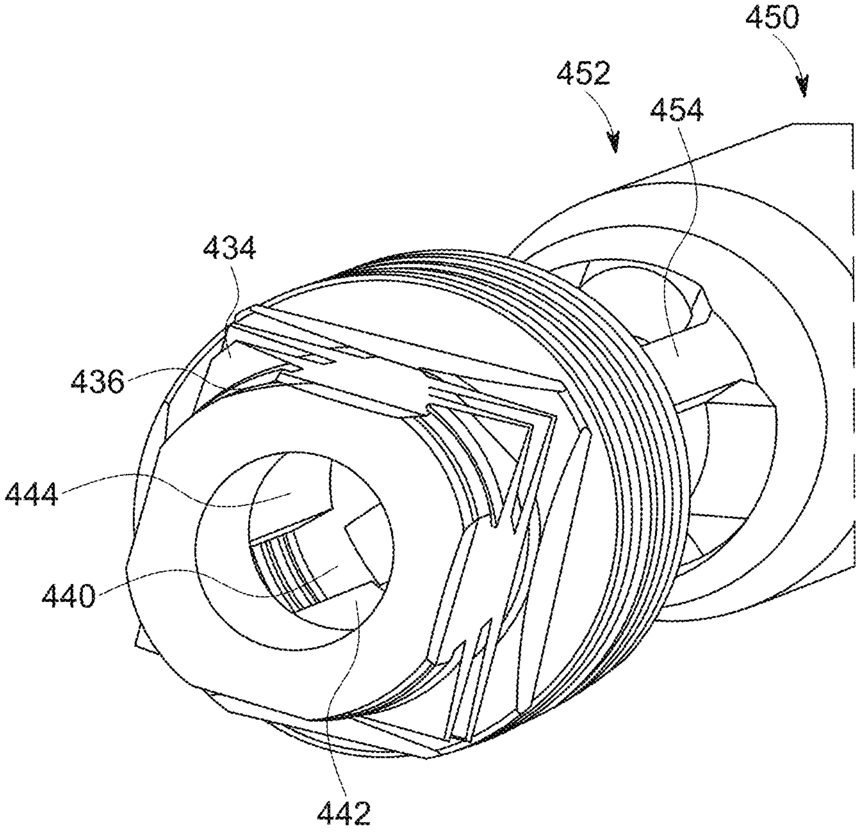
FIG. 10 is bottom end perspective view of the exemplary implant of FIG. 9 and instrument for facilitating soft tissue repair and/or reconstruction in conjunction with an implant system, in accordance with the present disclosure.

Referring now to FIGS. 9-10, an implant 400 is shown with an instrument 450 for implanting, manipulating, adjusting, and/or removing the implant 100. In some embodiments, the implant 400 may have one or more features the same as or similar to the implant 300 shown and described previously. Further, the instrument 450 may have one or more features the same as and/or similar to the instrument 350 as shown and described previously. The implant 400 includes a top portion 410, a bottom portion 430, and a body portion 420 arranged longitudinally between the top portion 410 and the bottom portion 430. The implant 400 is further shown to include a channel (e.g., a cannulated opening, cannulation, etc.) 440 extending along a longitudinal axis of the implant 400 from the proximal-most point of the top portion 410 through the body portion 420 and extending to and through the distal-most point of the bottom portion 430 thus establishing fluid communication in a longitudinal direction from the top portion 410 to and through the bottom portion 430 of the implant 400. The implant 400 is shown to include an interface feature 442 arranged within the channel 440 and, as shown in the exemplary embodiment of FIG. 10, disposed circumferentially about an inner surface 444 of the implant 400. The interface feature 442 of exemplary embodiment of the implant 400 shown in FIG. 10 includes four splines arranged circumferentially about the inner surface 444 of the implant 400 and extending along the inner surface 444 from the top portion 410 of the implant in a distal direction, with each of said splines positioned in approximately 90-degree increments (e.g., the splines are equally spaced circumferentially about the inner surface 444). In some embodiments, the interface feature 442 may include a greater or lesser number of splines, for example one, two, three, five, or another alternate number of splines. Further, the splines of the interface feature 442 may be arranged variously about the inner surface 444 of the implant 400, for example in some embodiments the splines may not have approximately equal spacing from one another as shown and described in FIGS. 9-10. In some embodiments, the splines may include a geometry other than that shown and described with reference to FIG. 10, for example the splines may include a substantially triangular geometry.

The interface feature 442 is configured to engage (e.g., receive, releasably couple with, etc.) one or more instruments that may be provided in a surgical kit along with the implant 400. As shown in FIG. 10, the instrument (e.g., a driver) 450 is shown to include an interface feature 454 arranged on a distal portion 452 of the instrument 450. The interface feature 454 of the instrument 450 is shown to be complimentary (e.g., geometrically opposite) to that of the interface feature 442. As shown in FIG. 10, the interface feature 454 of the instrument 450 includes four splines complimentary to those of the interface feature 442 of the implant 400. In some embodiments, the complimentary splines of the interface features 442, 454 may be configured to accommodate a greater torque than other similar geometries (e.g., torque from the instrument 450 being applied to the implant 400 so as to insert the implant 400 in the bone and/or soft tissue). The distal portion 452 of the implant 400 may be received (e.g., to engage, releasably couple, etc.) within the channel 440 of the implant 400 such that the interface feature 452 engages with the interface feature 442 along at least a portion of the length of the interior surface 444 of the channel 440. In some embodiments, the implant 400 may be produced and/or provided (e.g., as part of a sterile surgical kit) with the implant 400 in an engaged position such that the interface feature 442 of the implant 400 is engaged with the interface feature 454 of the instrument 400. In some embodiments, the interface feature 454 of the instrument 450 may include alternate geometries, for example, an alternate number of splines equivalent to that of the interface feature of the instrument 450. Further, in some embodiments the interface features 442, 454 may include alternate complimentary geometries (e.g., torx, hexagonal, etc.). Additionally, in some embodiments the interface features 442, 454 may be configured to provide a press fit between the instrument 450 and the implant 400. In some embodiments, this press fit may include feedback to the user, such as a haptic and/or audible "click" or other feedback to confirm engagement of the press fit feature. Further, the press fit feature may include one or more impressions or depressions arranged circumferentially around the inner surface 444 of the channel 440, with the complimentary (e.g., geometrically opposite) feature arranged circumferentially about the distal portion 452 of the instrument 450.

The implant 400 includes a threading 422 arranged on an outer surface 424 of the implant 400 and extending from a proximal-most portion of the top portion 410 to the distal-most portion of the body 420 of the implant. As shown in FIG. 9, the threading 422 is equally spaced (e.g., an equal spacing between threads when viewed from a side direction) along at least a portion of the length of the outer surface 424 of the implant 400. As shown in FIGS. 9-10, the threading 422 is a four-lobed thread, although the threading 422 may have other configurations in alternate embodiments. The implant 400 includes a plurality of flats 436 arranged on an outer surface 424 of the implant 400, with the flats 436 positioned at the distal-most portion of the body portion 420 and extending to the distal-most portion of the bottom portion 430. As shown, the implant 400 includes four flats 436, although alternate embodiments may have more or fewer flats 436. The flats 436 are shown to be arranged equidistant from one another about the circumference of the outer surface 424 of the implant but may be arranged alternatively in other embodiments. The implant 400 is further shown to include a tap feature 434 arranged at the proximal-most portion of the bottom portion 430 of the implant 400. As shown in FIGS. 9-10, the tap feature 434 includes a plurality of cutting flutes (e.g., four as shown in FIGS. 9-10, but greater or fewer cutting flutes in alternate embodiments) arranged circumferentially (e.g., in a singular lateral plane) about the outer surface 424 of the implant 400 and substantially equidistant from one another (e.g., approximately 90-degrees from one another). In alternate embodiments, the tap feature 434 may include one or more cutting flutes alternately arranged about the bottom portion 430 of the implant 400. The tap feature 434 is configured to facilitate implantation in the bone and/or soft tissue (including, for example, especially dense bone) without requiring additional instruments or tools (e.g., a drill to create a pilot hole, etc.). Accordingly, a physician may insert the implant 400 via the tap feature 434 into a bone in a time-efficient and instrument-efficient manner (which does not require obtaining and switching between multiple instruments). In some embodiments, the tap feature 434 may include geometries other than the square geometry shown and described with reference to FIGS. 9-10. The bottom portion 430 of the implant 400 is further shown to include a tip 432 arranged at the distal-most portion of the bottom portion 430. The tip 432 is shown to have a substantially cylindrical geometry, with the cylindrical geometry diametrically equal to or lesser than that of the body portion 420 and the top portion 410.

The implant 400 is further shown to include a plurality of vents (e.g., openings) 426 positioned on the outer surface 424 of the implant 400. As shown in the exemplary embodiment of FIG. 9, the vents 426 extend from the proximal-most portion of the top portion 410 to the distal-most portion of the body 420. The implant 400 as shown includes four vents 426 arranged circumferentially about the outer surface 424 of the implant 400 and substantially equidistant from one another (e.g., at approximately 90-degree increments). The vents 426 are shown to extend from the outer surface 424 of the implant to the inner surface 444 of the implant, thus establishing fluid communication between the outer surface 424 of the implant 400 and the channel 440. It should be noted that the vents 426 are arranged so as not to interfere with the interface feature 442 and that the interior surface 444 of the implant 400 may include alternating vents 426 and splines of the interface feature 442 arranged circumferentially within the channel 440. Further, the vents 426 may be configured to align with one or more openings or other components (e.g., recesses) of the instrument 450 when in an engaged position (as shown in FIG. 10). After implantation, the vents 426 are configured to facilitate bone ingrowth thus providing additional fixation within the bone and/or soft tissue. In some embodiments, the implant 400 may have greater or fewer than the four vents 426 shown in FIG. 9, where the vents 426 may be arranged alternately (e.g., not equidistant circumferentially from one another) about the outer surface 424 of the implant 400. The threading 422 is shown to extend around the body portion 420 from the bottom portion 430 to the top portion 410, with the threading 422 traversing the vents 426 as shown in FIG. 9.

Figure 11:
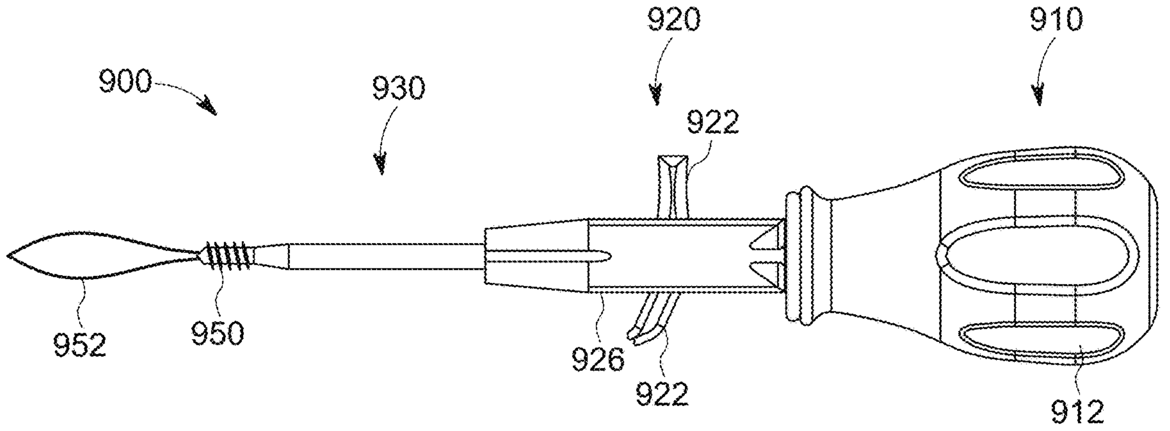
FIG. 11 is a side view of an exemplary instrument for facilitating soft tissue repair and/or reconstruction in conjunction with an implant system, in accordance with the present disclosure.
Figure 12:
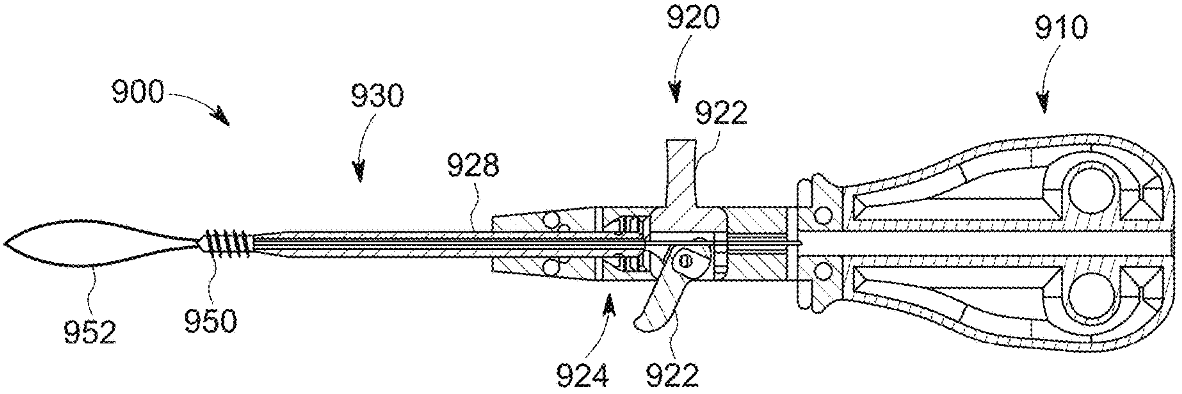
FIG. 12 is a side cross-sectional view of the exemplary instrument of FIG. 11 for facilitating soft tissue repair and/or reconstruction in conjunction with an implant system, in accordance with the present disclosure.
Figure 13:
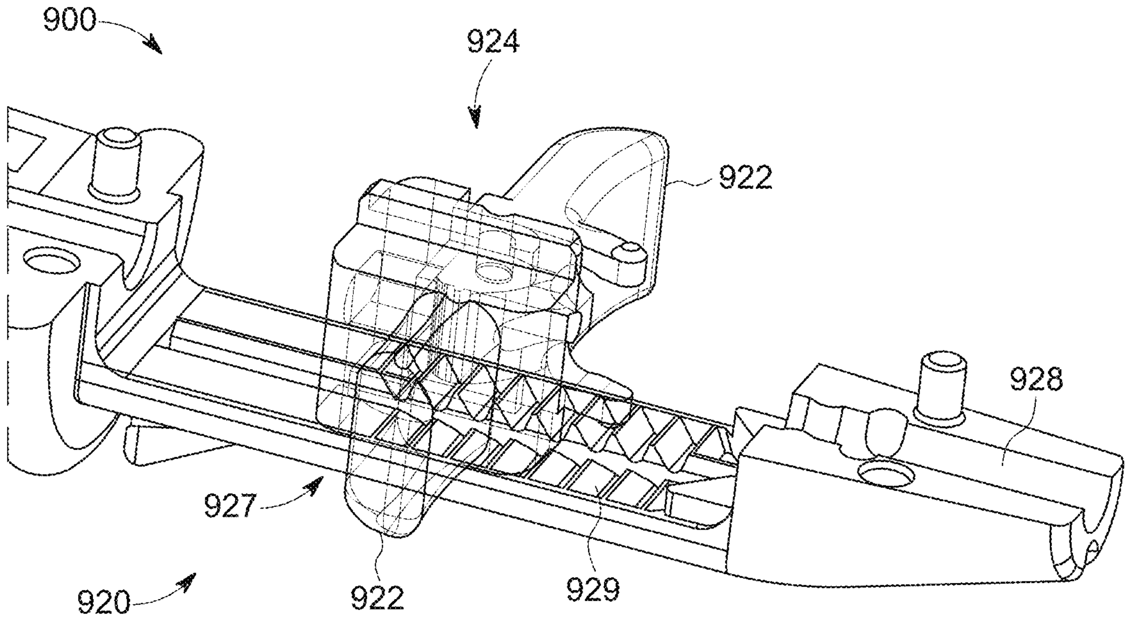
FIG. 13 is a perspective view of a portion of the exemplary instrument of FIGS. 11-12 for facilitating soft tissue repair and/or reconstruction in conjunction with an implant system, in accordance with the present disclosure
Figure 14:
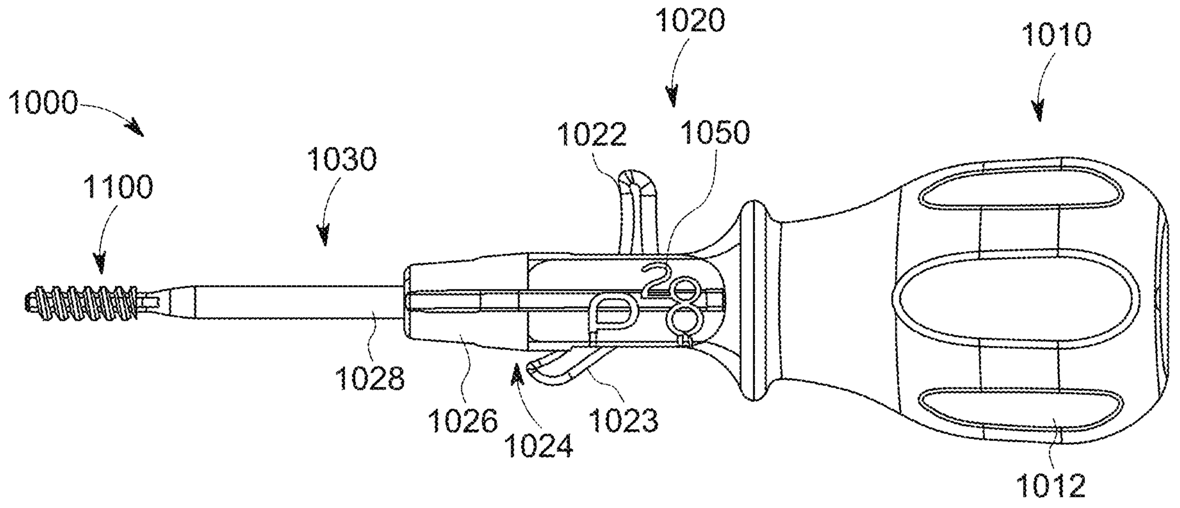
FIG. 14 is a side view of an exemplary instrument for facilitating soft tissue repair and/or reconstruction in conjunction with an implant system, in accordance with the present disclosure.
Figure 15:
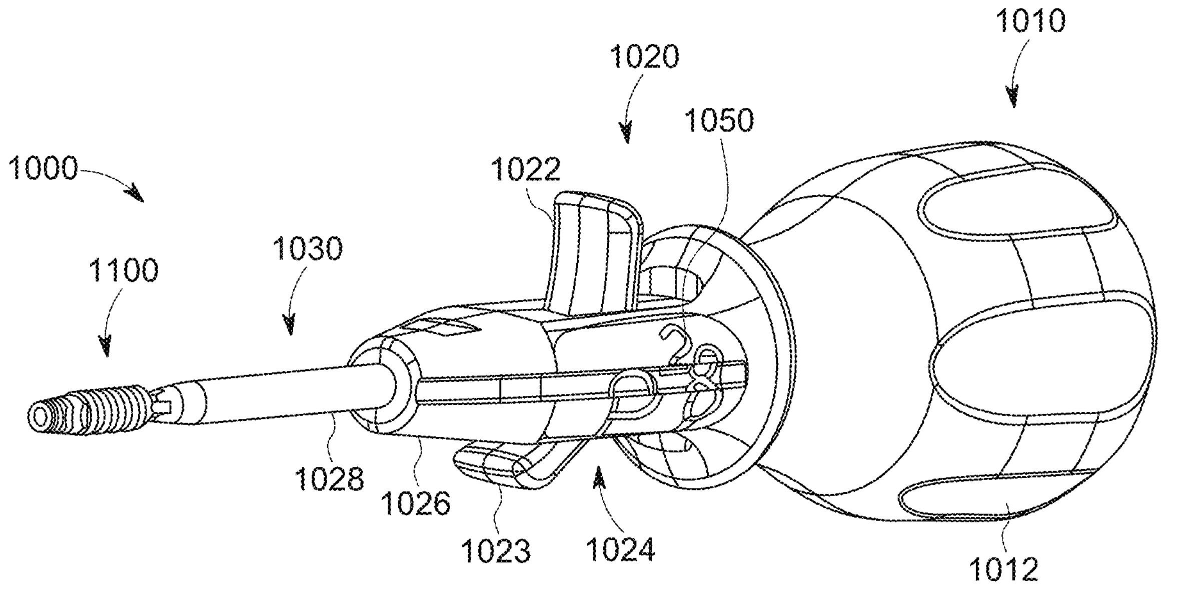
FIG. 15 is a side, front, perspective view of the exemplary instrument of FIG. 14 for facilitating soft tissue repair and/or reconstruction in conjunction with an implant system, in accordance with the present disclosure.

Referring now to FIGS. 11-13, an instrument 900 is shown. The instrument 900 is shown to include a handle 910 and an extension 930 arranged opposite the instrument 900 from the handle 910. The instrument 900 is further shown to include a body portion 920 arranged between the handle 910 and the extension 930. The handle 910 is shown to have a substantially cylindrical shape with one or more depressions 912 arranged about the surface of the handle 910 (as shown, circumferentially). In some embodiments, the depressions 912 may be configured to facilitate grip of the instrument 900 when applying torque or other force to the instrument 900 (for example, when driving an anchor or implant into the soft tissue and/or bone).

The body portion 920 is shown to include a mechanism 924 and a pair of arms 922, with the arms 922 arranged substantially opposite the body portion 920 one another and extending from the body portion 920 in substantially opposite directions. The mechanism 924 as shown in FIGS. 12-13 is a cam lever mechanism loaded by a resilient member (e.g., a spring), although in other embodiments alternative mechanisms may be implemented. The mechanism 924 is configured within a housing 926. The mechanism 924 is configured to retain (e.g., contact, restrict, hold, etc.) a suture 952 that is threaded through an implant 950. The suture 952 and implant 950 may be the same as or similar to those shown and described previously herein. One of the pair of arms 922 is configured to permit tensioning of the suture 952 by manipulating the arm toward the handle 910. The suture 952 extends from the implant 950 along a track 928 extending substantially along a longitudinal axis of the instrument from the distal-most portion of the extension into the housing 926 of the body portion 920. The mechanism 924 includes a ratchet 927 as shown in FIG. 13 which is configured to facilitate the tensioning of the suture 952 by manipulation of the mechanism 924 via one of the pair of arms 922. The ratchet 929 allows the tensioning of the suture 952 at discrete intervals according to manipulation of the mechanism 924 as the ratchet 927 in manipulated about a set of cam lever teeth 927. The instrument 900 may be configured to hold up to approximately 50 lbf. of tension in the suture 952, which is greater than the estimated tension that a physician could manually apply (approximately 20 lbf). Tensioning of the suture 952 beyond that which is reasonably obtained manually is desirable in repairing and/or reconstructing soft tissue injuries. As the implant 950 is inserted into the bone and/or soft tissue by a physician using the instrument 900, the ratchet 927 is overcome and the tension of the suture 952 is released. Alternatively, a physician may manually release tension in the suture 952 by manipulating one of the pair of arms 922 toward the implant 900 (e.g., opposite direction of the handle 910).

Referring now to FIGS. 14-17, an instrument 1000 is shown. The instrument 1000 is shown to include a handle 1010 and an extension 1030 arranged opposite the instrument 1000 from the handle. The instrument is further shown to include a body portion 1020 arranged between the handle 1010 and the extension 1030. The handle 1010 is shown to have a substantially cylindrical shape with one or more depressions 1012 arranged about the surface of the handle 1010 (as shown, circumferentially). In some embodiments, the depressions 1012 may be configured to facilitate the grip of the instrument 1000 when applying torque or other force to the instrument 1000 (for example, when driving an anchor or implant into soft tissue and/or bone).

Figure 16:
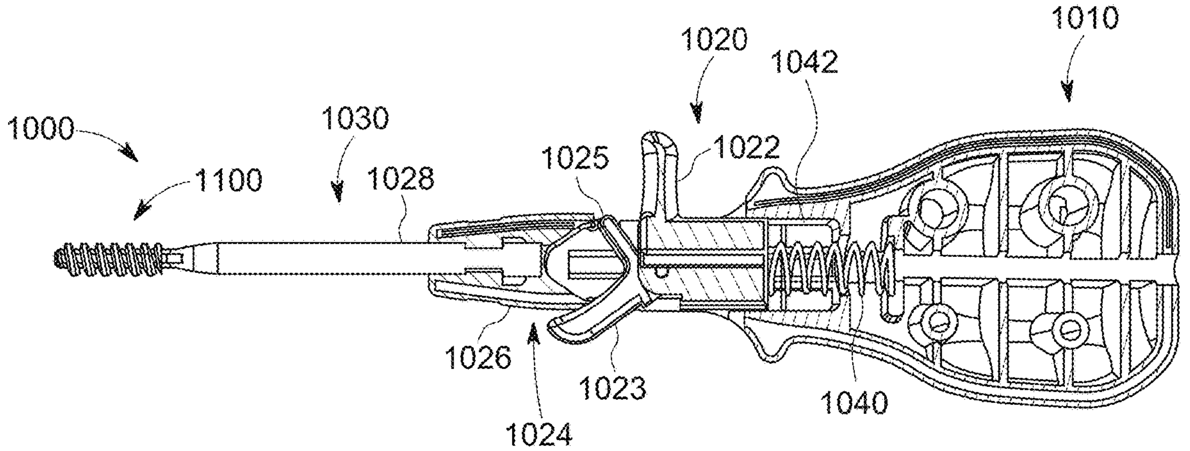
FIG. 16 is a side, cross-sectional view of the exemplary instrument of FIG. 14 for facilitating soft tissue repair and/or reconstruction in conjunction with an implant system, in accordance with the present disclosure.
Figure 17:
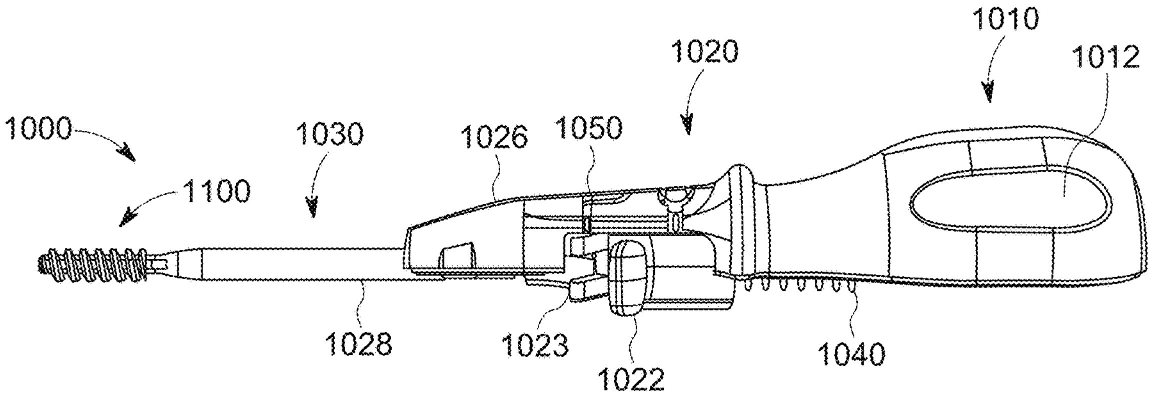
FIG. 17 is a cutaway top view of the exemplary instrument of FIG. 14 for facilitating soft tissue repair and/or reconstruction in conjunction with an implant system, in accordance with the present disclosure.

The body portion 1020 is shown to include a mechanism 1024 as well as a first arm 1022 and a second arm 1023, wherein the first and second arms 1022, 1023 are arranged substantially opposite the body portion 1020 and extending from the body portion 1022 in substantially opposite directions. As shown in FIG. 16, the second arm 1023 is configured to be pivotable about a coupling point with the first arm 1022. The first arm 1022 may be static and configured to be gripped by a user (e.g., physician) in order to manipulate the instrument 1000. The mechanism 1024 as shown in FIGS. 14-17 is a tensioning mechanism including a resilient member 1040, shown in the exemplary embodiment of FIGS. 14-17 as a spring (although in other embodiments alternative mechanisms may be implemented). The mechanism 1024 is configured without a housing 1026. The mechanism 1024 is configured to retain (e.g., contact, restrict, hold, etc.) a suture (not shown) that is threaded through the implant 1100. Although not shown, the suture may be the same as and/or similar to that shown previously in conjunction with the instrument 900 and the implant 950. The second arm 1023 is shown to be manipulatable (e.g., can be actuated so as to engage the resilient member 1040) by a user so as to engage the mechanism 1024 and components thereof in order to tension a loaded suture. The second arm 1023 is shown to include an engagement portion 1025 configured adjacent to a track 1050 (e.g., a continuous depression disposed on at least a portion of an outer surface of the instrument), where the track 1050 is configured to route the suture from the exterior of the instrument 1000 to the interior adjacent the mechanism 1024 (and within the housing 1026). As shown, the track 1050 has a footprint similar to a "Paragon 28" or "P28" logo, but may be modified to other footprints/configurations of various geometries and sizes. Manipulation of the second arm 1023 is shown to retain/release the suture in conjunction with the mechanism 1024 so as to enable tensioning of the suture. In some aspects, the second arm 1023 is configured to be manipulated (while the first arm 1022 is gripped to provide leverage) so as to tension the suture at discrete intervals according to the manipulation of the mechanism 1024.

As shown in FIGS. 14-17, the first and second arms 1022, 1023 may be manipulated in a direction toward the handle 1010 so as to drive compression of the resilient member 1040 (and thus releasing any tension in the suture). Conversely, when the first and second arms 1022, 1023 are not actuated toward the handle 1010, the suture may be in a tensioned or active state. The instrument 1000 may be configured to hold up to approximately 50 lbf. of tension in the suture, which is greater than the estimated tension that a physician could manually apply (approximately 20 lbf). Tensioning of the suture beyond that which is reasonably obtained manually is desirable in repairing and/or reconstructing soft tissue injuries. In some aspects, as the implant 1100 is inserted into the bone and/or soft tissue by a physician using the instrument 1000, the mechanism 1024 is overcome and tension of the suture may be released. Alternatively, a physician may manually release the tension in the suture by manipulating the second arm 1023 away from the implant 1100 (e.g., toward the direction of the handle 1010) such that the engagement portion 1025 disengages with the suture.

Figure 18:
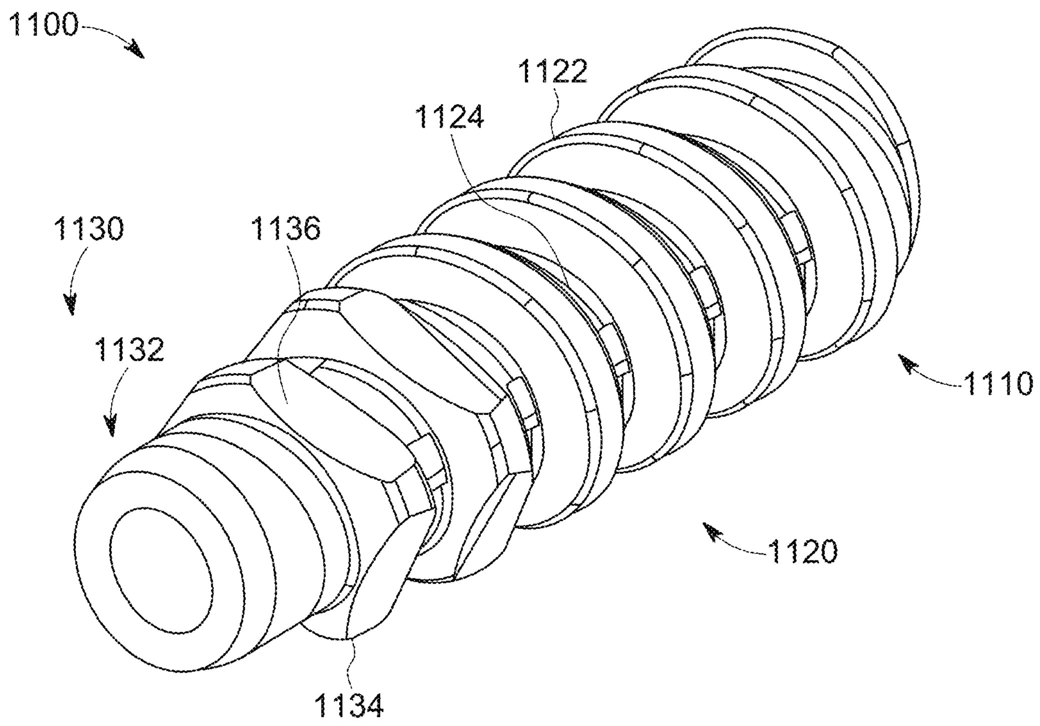
FIG. 18 is a front end perspective view of an exemplary implant for facilitating soft tissue repair and/or reconstruction in conjunction with an implant system, in accordance with the present disclosure.
Figure 19:
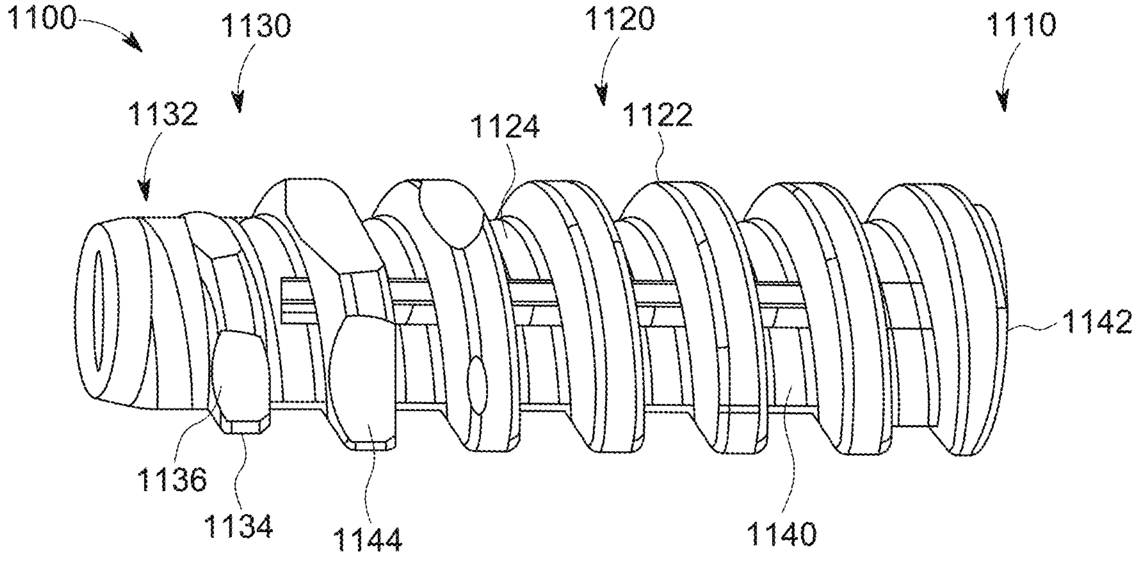
FIG. 19 is a side view of the exemplary implant of FIG. 18 for facilitating soft tissue repair and/or reconstruction in conjunction with an implant system, in accordance with the present disclosure.

Referring now to FIGS. 18-19, an exemplary embodiment of an implant 1100 is shown. It should be understood that the implant 1100 may have one or more features, geometries, or other properties the same as and/or similar to that of other exemplary implants shown and described previously herein. Similarly, the implant 1100 may be compatible with one or more of the implants and/or instruments shown and described herein (e.g., may be a component of a system including one or more other components shown and described herein). The implant 1100 is shown to include a top portion 1110, a bottom portion 1130, and a body portion 1120 arranged between the top portion 1110 and the bottom portion 1130. The implant 1100 is further shown to include a channel (e.g., a cannulated opening) 1140 extending along a longitudinal axis of the implant 1100 from the proximal-most point of the top portion 1110 through the body portion 1120 and extending through the distal-most point of the bottom portion 1130. The implant 1100 is shown to include an interface feature 1142 arranged within the channel 1140 which may be the same as and/or similar to that of one or more other implants shown and described previously herein, (e.g., the exemplary embodiment of FIGS. 2-4), disposed circumferentially about an inner surface 1144 of the implant 1100.

The interface feature 1142 is configured to engage (e.g., receive, releasably couple with, etc.) one or more instruments that may be provided in a surgical kit along with the implant 1100. The implant 1100 may be configured to engage with the instrument 250 shown previously in the same or a similar manner to that of the implant 200. Alternatively, the implant 1100 may be configured to interface with other similar instruments or may also have compatibility with various instruments and/or various common coupling geometries or sizes (e.g., Torx, etc.).

The implant 1100 includes a threading 1122 arranged on an outer surface 1124 of the implant 1100 and extending from a proximal-most portion of the top portion 1110 to the bottom portion 1130 of the implant. As shown in FIGS. 18-19, the threading 1122 is equally spaced (e.g., an equal spacing between threads when viewed from a side direction) along the length of the outer surface 1124 of the implant 1100. The threading 1122 may, in some aspects, be a four-lobed thread, or may have other configurations in alternate embodiments. Similarly, in some aspects the threading 1122 may have a self-tapping configuration. The implant 1100 is further shown to include a plurality of vents (e.g., openings) 1126 positioned on the outer surface 1124 of the implant 1100. As shown in the exemplary embodiment of FIGS. 18-19, the vents 1126 extend from the proximal-most portion of the top portion 1110 to the distal-most portion of the body 1120. The implant 1100 as shown includes the vents 1126 arranged circumferentially about the outer surface 1124 of the implant 200 and substantially equidistant from one another and may vary in quantity and spacing from one another (e.g., at approximately rotational degree increments of 90-degrees, 180-degrees, etc.). The vents 1126 are shown to extend from the outer surface 1124 of the implant 1100 to the inner surface 1144 of the implant 1100, thus establishing fluid communication between the outer surface 1124 of the implant 1100 and the channel 1140. It should be noted that the vents 1126 are arranged so as not to interfere with the interface feature 1142 and that the inner surface 1144 of the implant 1100 may include alternating vents 1126 and splines of the interface feature 1142 arranged circumferentially within the channel 1140. Further, the vents 1126 may be configured to accommodate an instrument, for example to align with the openings 256 of the instrument 250 when in an engaged position. After implantation, the vents 1126 are configured to facilitate bone ingrowth thus providing additional fixation within the bone and/or soft tissue. In some embodiments, the implant 1100 may have greater or fewer than the four vents 1126 shown in FIGS. 18-19, where the vents 1126 may be arranged alternately (e.g., not equidistant circumferentially from one another) about the outer surface 1124 of the implant 1100. The threading 1122 is shown to extend around the body portion 1120 from the bottom portion 1130 to the top portion 1110, with the threading 1122 traversing the vents 1126.

The implant 1100 includes a tip 1132 arranged at the distal-most portion of the bottom portion 1130. The tip 1132 is shown to have a substantially cylindrical geometry, but may have alternate geometries in other embodiments. The tip 1132 is shown to include a tap feature 1136 shown as a square tap in the exemplary embodiment of FIGS. 18-19. The tap feature 1136 is configured to facilitate implantation in bone and/or soft tissue (including, for example, especially dense bone) without requiring additional instruments or tools (e.g., a drill to create a pilot hole, etc.). Accordingly, a physician may insert the implant 1100 via the tap feature 1136 into the bone in a time-efficient and instrument-efficient manner (which does not require obtaining and switching between multiple instruments). In some embodiments, the tap feature 1136 may include geometries other than the square geometry shown and described with reference to FIGS. 18-19. Further, in some embodiments (and depending on the material of which the implant 1100 consists of), the tip 1132 that is adjacent to the tap feature 1136 may include cutting flutes configured to facilitate the implantation (for example, a metal embodiment may include cutting flutes, whereas a PEEK embodiments may include a square tap feature 1136 as shown).

The implant 1100 may have one or more standard lengths, with the length measured from the proximal-most point of the top portion 1110 to the distal-most portion of the bottom portion 1130. For example, the implant 1100 may have a length ranging from 2 mm to 6 mm, with various different sized produced and/or provided in a surgical kit in increments of 0.5 mm. Additionally, the embodiment of the implant 1100 shown in FIGS. 18-19 may be available in multiple lengths (e.g., as components of a surgical kit or independently) so as to accommodate different applications of implantation into the bone and/or soft tissue to facilitate repair and/or reconstruction of the soft tissue. Further, the implant 1100 may have a standard diameter and/or may be available in various different diameters so as to accommodate different applications of implantation into the bone and/or soft tissue to facilitate the repair and/or reconstruction of the soft tissue. Such various diameters may be components of a surgical kit (e.g., a sterile kit including multiple lengths and diameters of the implant 1100 as well as other components, for example one or more k-wires, drills, and/or drivers) and/or may be available independently of the a kit. The implant 1100 may be formed of a metal (e.g., titanium), or one or more forms of PEEK (e.g., HA Peek, carbon fiber reinforced PEEK, HA/CF PEEK, natural PEEK, etc.) and/or other polymers. In some aspects, the implant 1100 may be produced and/or provided with a suture (e.g., those shown and described in the patent applications referenced previously, or other similar sutures and/or suture tapes) threaded through the openings 1134. Further, in some aspects the implant 1100 may be produced and/or provided (e.g., in a sterile surgical kit) in a pre-loaded state, where the implant 1100 is engaged with the instrument 250 and a suture as described previously threaded through the implant 1100.

Any of the implants and/or instruments disclosed herein may be implemented according to the following exemplary technique for a soft tissue repair and/or reconstruction. Additionally, one or more of the steps included herein may be repeated, skipped, or performed in an alternate order in the process of repairing and/or reconstructing soft tissue.

In performing a soft tissue repair and/or reconstruction, a physician may place a k-wire or other stabilization component corresponding to a first implant to be placed. The physician may then confirm placement of the k-wire using x-ray or other imaging techniques. The physician may then drill or otherwise form a pilot hole corresponding to a desired implant diameter. The physician may then obtain a pre-loaded (e.g., engaged) implant which is engaged with an instrument (where the implant and/or instrument may be threaded with one or more sutures, or the physician may pass a suture through the implant and instrument). The physician may then center the suture tape on the tip of the implant. The physician may then insert the implant into the bone and/or soft tissue. The physician may then prepare an additional pilot hole for an additional implant. The physician may then pass a first portion of a suture from the first implant through a second implant using a suture passer (or the second implant may already be threaded with suture common to the first implant). The physician may then place a portion of the second implant at least partially into the pilot hole. The physician may then manually remove slack from one or more sutures. The physician may then tension the suture between the first implant and second implant using an instrument (e.g., the tensioning instrument shown and described herein). The physician may then insert the implant so as to lock tension of the suture. The physician may then repeat the steps of creating a pilot hole to locking the tension on the suture with a third implant and/or additional implants. When the physician has implanted a desired number of implants and locked in the desired tension of the suture(s), the physician may tie off or trim any excess suture length.

Figure 20:
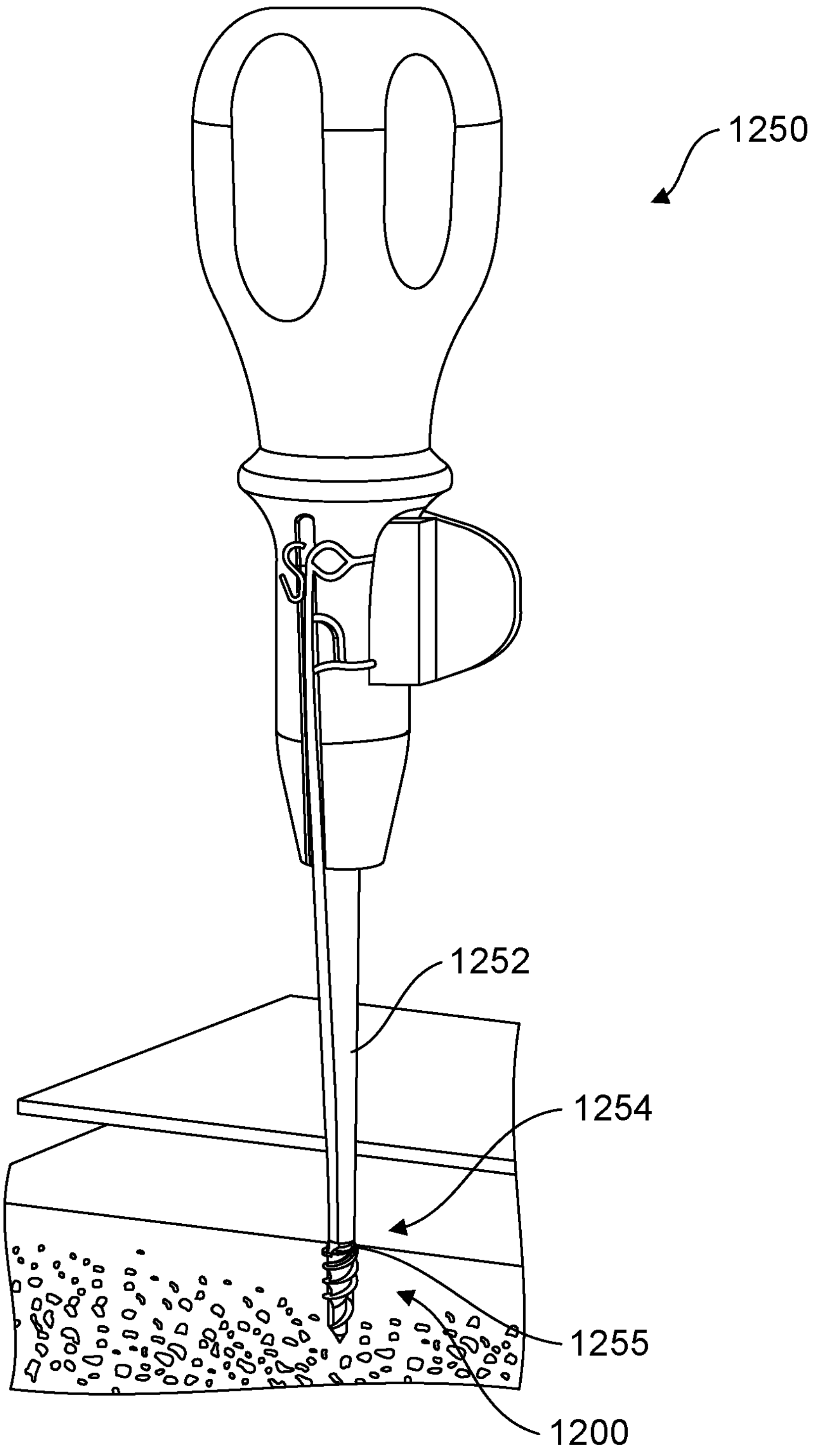
FIG. 20 is a front perspective view of an exemplary implant and instrument for facilitating soft tissue repair and/or reconstruction in conjunction with an implant system, in accordance with the present disclosure.
Figure 21:
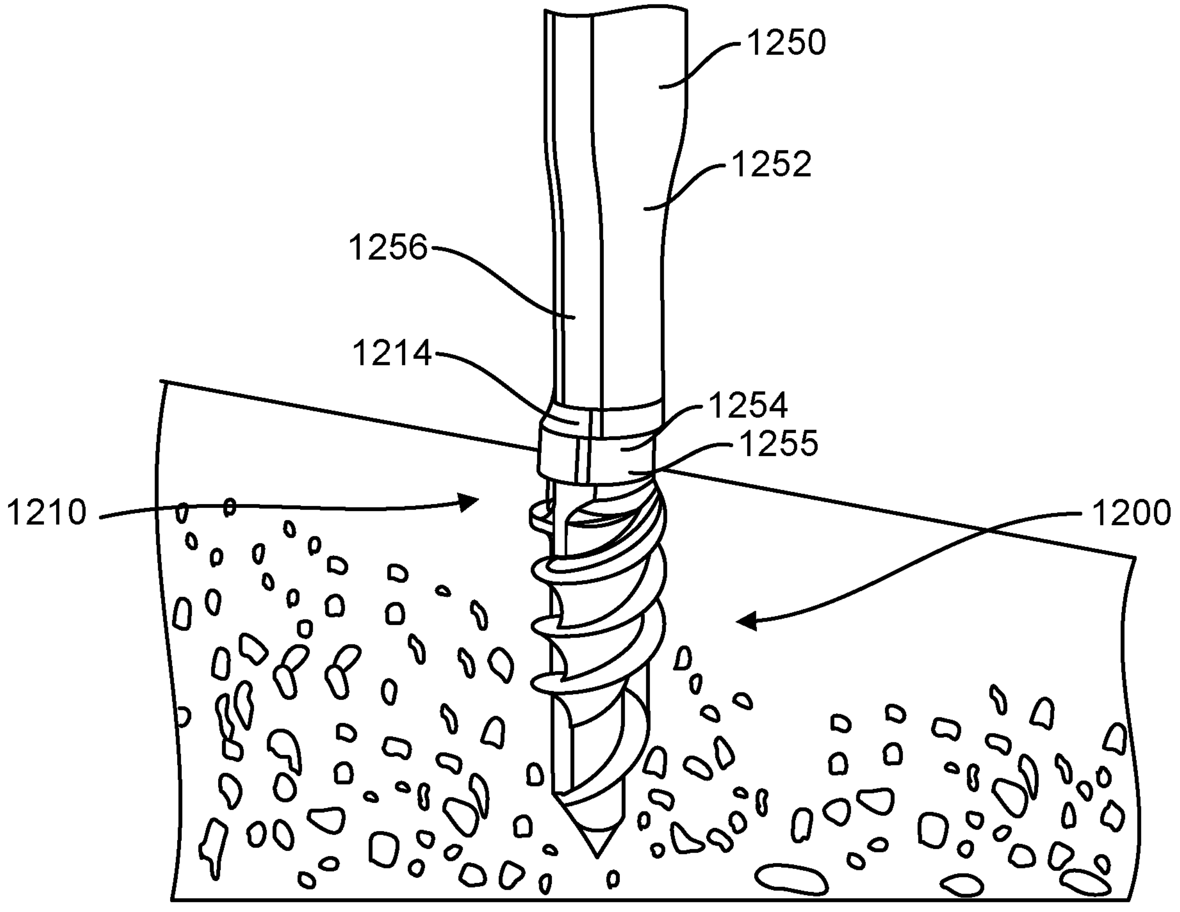
FIG. 21 is a front perspective view of the exemplary implant and a distal portion of the exemplary instrument of FIG. 20 for facilitating soft tissue repair and/or reconstruction in conjunction with an implant system, in accordance with the present disclosure.

Referring now to FIGS. 20-46, there is illustrated an exemplary embodiment of an implant 1200 (e.g., anchor, etc.) for fixation within bone and/or soft tissue so as to facilitate repair and/or reconstruction of soft tissue. Also shown in FIGS. 20-21 is an instrument 1250 configured to engage with and/or facilitation the implantation, manipulation, adjustment, and/or removal of the implant 1200 (which may be components of a system). The implant 1200 is shown to include a top portion 1210 and a bottom portion 1230, with a body portion 1220 disposed between the top portion 1210 and the bottom portion 1230. The top portion 1220 of the implant 1200 is shown to include a head 1212 arranged at the proximal end of the top portion 1210 of the implant 1200. As shown in the exemplary embodiment of FIGS. 20-46, the head 1212 includes an interface feature 1214 positioned at the proximal end of the top portion 1210. The interface feature 2114 is configured to engage (e.g., interface, releasably couple with, receive a portion of, etc.) with at least a portion of the instrument 1250. The instrument 1250 is shown to include an interface feature 1254 arranged on a distal portion 1252 of the instrument 1250, with the interface feature 1254 having a complimentary geometry to that of the interface feature 1214 of the implant 1200. Further, the instrument 1250 is shown to include a recess 1256 arranged on the distal portion 1252 of the instrument 1250. The recess 1256 is shown to include at least a portion of the substantially cylindrical geometry of the distal portion 1252 and may be configured to align with one or more portions of the implant 1200 to facilitate threading of one or more needles and/or sutures.

As shown in the exemplary embodiment of FIGS. 20-46, the interface feature 1214 is shown to include a pair of arc-shaped protrusions 1218 ("protrusions 1218") on opposite sides of the head 1212 and separated (and connected) by a bridge 1217 extending therebetween. The bridge 1217 may have a linear geometry, or may be tapered in one or more directions along a length and/or width thereof. In some embodiments, as shown in FIGS. 30-41, the bridge portion 1217 may have one or more grooves in sides thereof, such as diametrically opposed grooves on opposing sides of the bridge portion 1217. As also as shown in FIGS. 30-41, the body portion 1220 of the implant 1200 may include grooves or apertures (that are aligned with, and/or extend from, the grooves of the head portion 1210 in the bridge portion 1217 within the voids 1219) that extend to an opening 1216, as discussed further below.

The protrusions 1218 are symmetrical to one another and are diametrically opposed from one another relative to the head 1212. Further, the protrusions 1218 are shown to have a semi-circular arc-shaped geometry such that the pair of protrusions 1218 collectively form less than a 360-degree arc (e.g., a complete circle). Accordingly, the interface 1214 is further shown to include a pair of voids 1219 positioned between the protrusions 1218 and diametrically opposed from one another 9 (bounded by a side of the bridge portion 1217 and inner sides of the protrusions 1218). In engaging with the interface feature 1254 of the instrument 1250, one or more protrusions 1255 of the interface feature 1254 may be positioned within each of the voids 1219 such that said protrusions 1255 of the interface feature 1254 are positioned adjacent the protrusions 1218. Accordingly, the protrusions 1218 may occupy one or more recesses 1256 of the interface feature 1254 such that the protrusions 1218 are positioned adjacent the aforementioned protrusions of the interface feature 1254.

Accordingly, during such engagement between the interface feature 1254 and the interface 1214, the outer surfaces of the protrusions 1218 and the protrusions 1255 may collectively form a circumferential surface where the protrusions 1218 and 1255 are flush when adjacent one another in the engaged position. As shown in FIGS. 20-21, the flush configuration permits insertion of the distal portion 1252 within a bore formed within a bone, as the lateral dimension of the engaged instrument-implant construct is not greater than that of the implant itself. Accordingly, the implant 1200 may be inserted within a bore formed in a bone, with the instrument 1250 twisted so as to engage the threading 1222 with said bone. As the implant 1200 is advanced into the bone, it may be positioned such that the top surface of the protrusions 1218 is positioned below the top surface of the bone while engaged with the instrument 1250. In alternate embodiments, the interface feature 1214 may have alternate geometries, for example a traditional torx geometry, a hexagonal geometry or various geometries with one or more splines arranged variously about the interface feature 1214. Accordingly, such alternate geometries of the interface feature 1214 may be configured to accommodate a portion of one or more instruments as mentioned previously, for example a driver or other instrument.

The top portion 1210 is further shown to include an opening (e.g., an aperture, eyelet, etc.) 1216 configured to receive a suture threaded through said opening 1216. As shown in the exemplary embodiment of FIGS. 20-46, the opening 1216 is defined in lateral directions by at least a portion of the interface feature 1214, and in a distal direction by at least a portion of the body portion 1220. In some aspects, the opening 1216 may be disposed at least partially within the body portion 1220 and have an elongated cross-sectional geometry. In some embodiments, a bottom end or side of the opening 1216 may be (smoothly) arcuately concave.

The opening 1216 may be arranged such that when the implant 1214 interfaces with the instrument 1250 such as those previously mentioned, the opening 1216 is aligned with and/or positioned adjacent at least a portion of one or more openings or recesses of said instruments (e.g., the recess 1256 of the instrument 1250). For example, the instrument 1250 may include a shaft with diametrically opposed openings with which the opening 1216 may align when the implant 1200 engages with the instrument 1250 via at least the interface feature 1214. The alignment of the openings of the instrument 1250 with the opening 1216 of the implant 1200 may be configured to facilitate threading of a suture through one opening of the instrument 1250, through the opening 1216 of the implant 1200 engaged with the instrument 1250, and subsequently through a second opening of the instrument 1250. Such threading of a suture through the opening 1216 engages the suture with the implant 1200 prior to implantation and further allows for the implant 1200 to be implanted within bone and/or soft tissue without requiring an intermediate step to thread the suture after implantation has been initiated. Following implantation, the instrument 1250 may be disengaged from the interface feature 1214 of the implant 1200 and the suture, with the suture then free to be secured and/or manipulated as needed (e.g., coupled with one or more other implants, tensioned, etc.).

Figure 22:
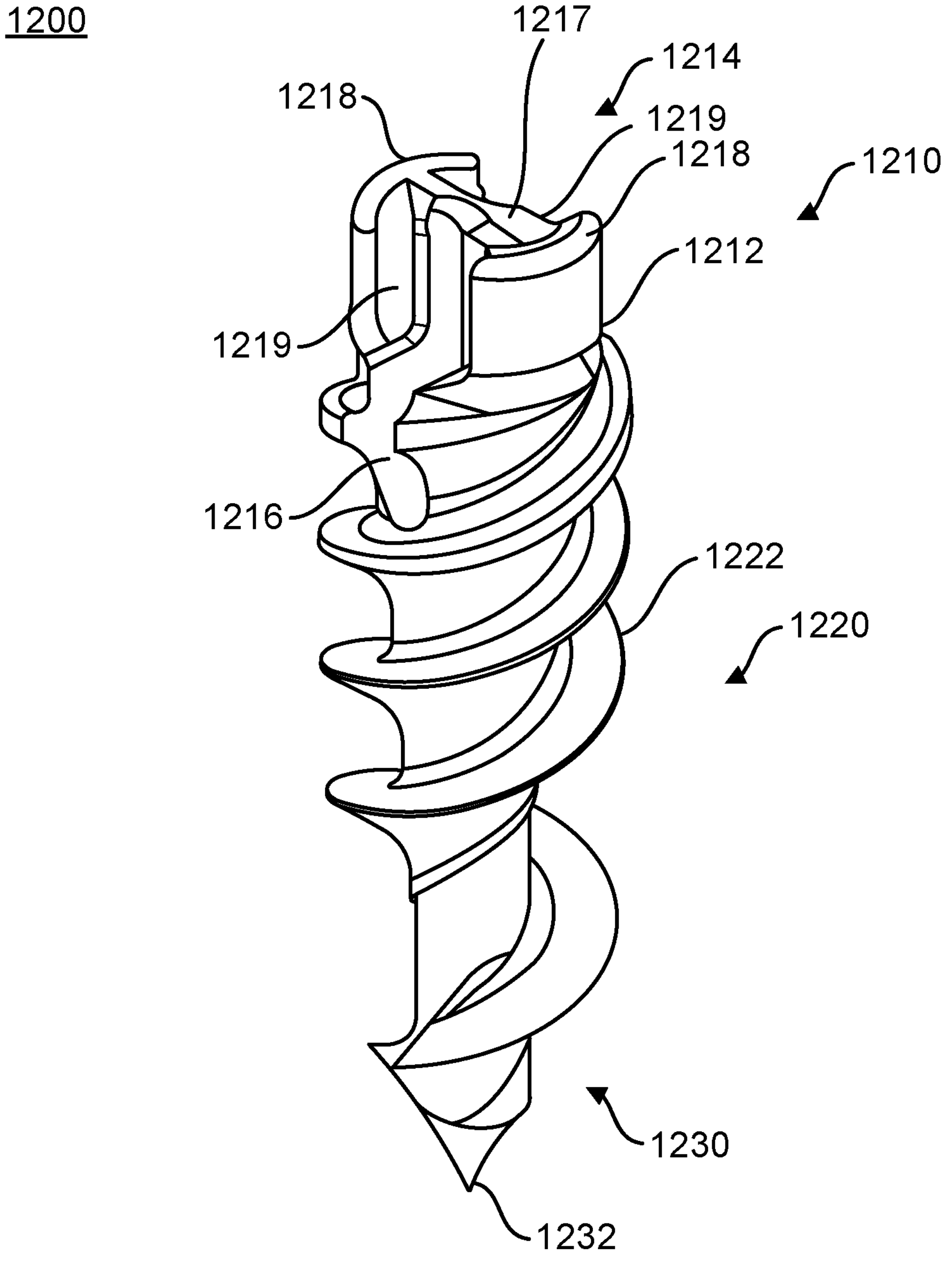
FIG. 22 is a front right perspective view of the exemplary implant of FIG. 21 for facilitating soft tissue repair and/or reconstruction in conjunction with an implant system, in accordance with the present disclosure.
Figure 23:
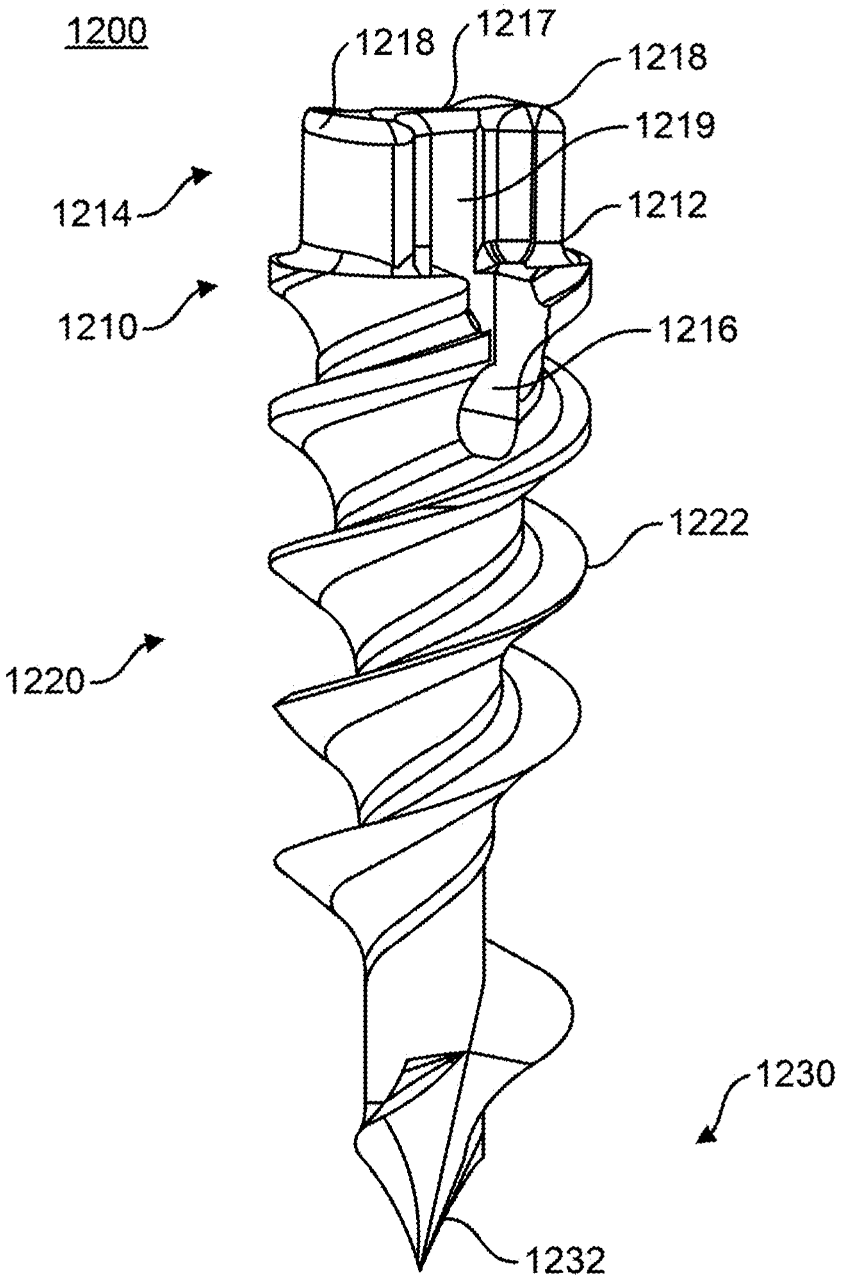
FIG. 23 is a front left perspective view of the exemplary implant of FIG. 22 for facilitating soft tissue repair and/or reconstruction in conjunction with an implant system, in accordance with the present disclosure.
Figure 24:
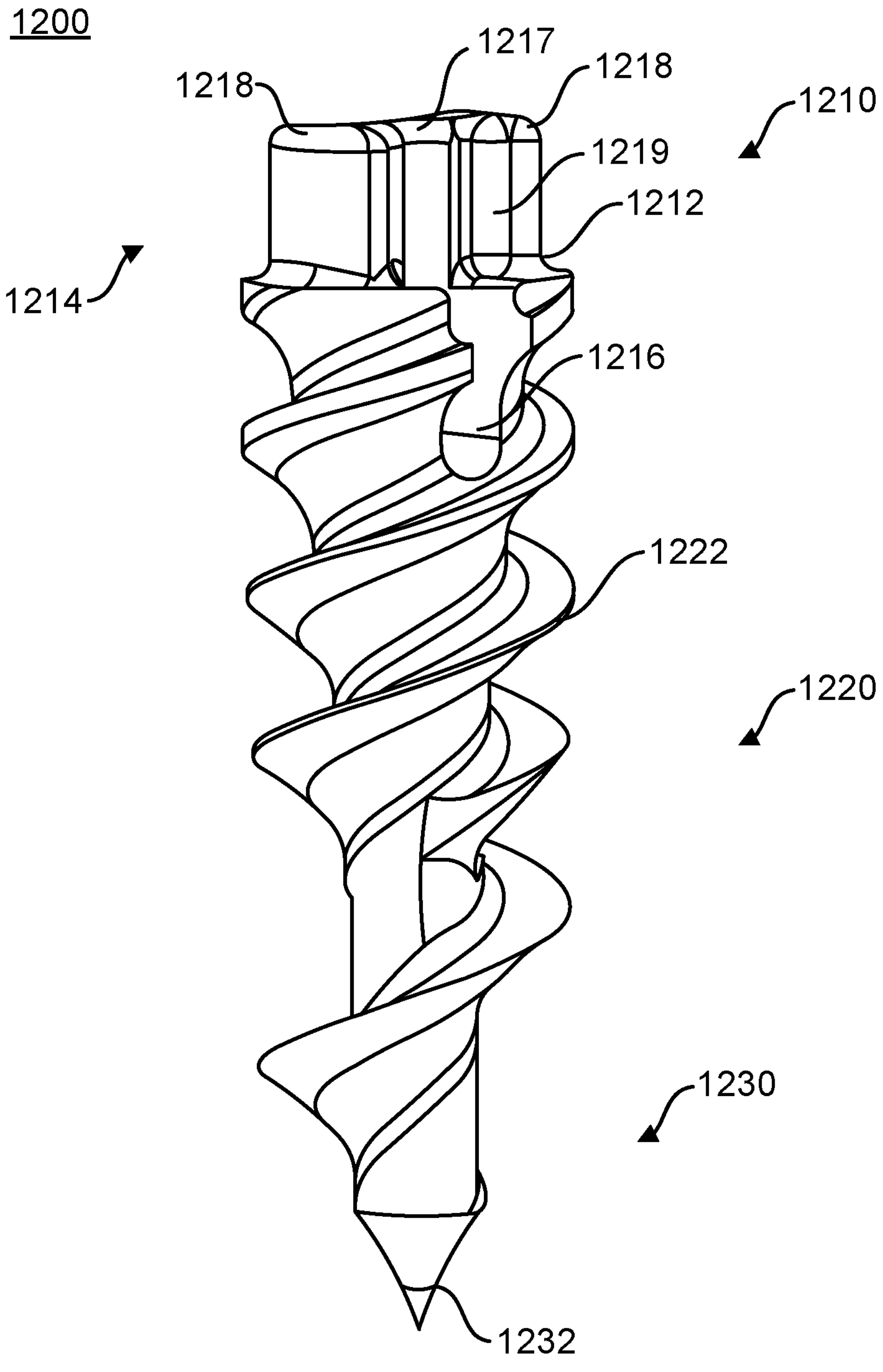
FIG. 24 is a rear right perspective view of the exemplary implant of FIG. 22 for facilitating soft tissue repair and/or reconstruction in conjunction with an implant system, in accordance with the present disclosure.
Figure 25:
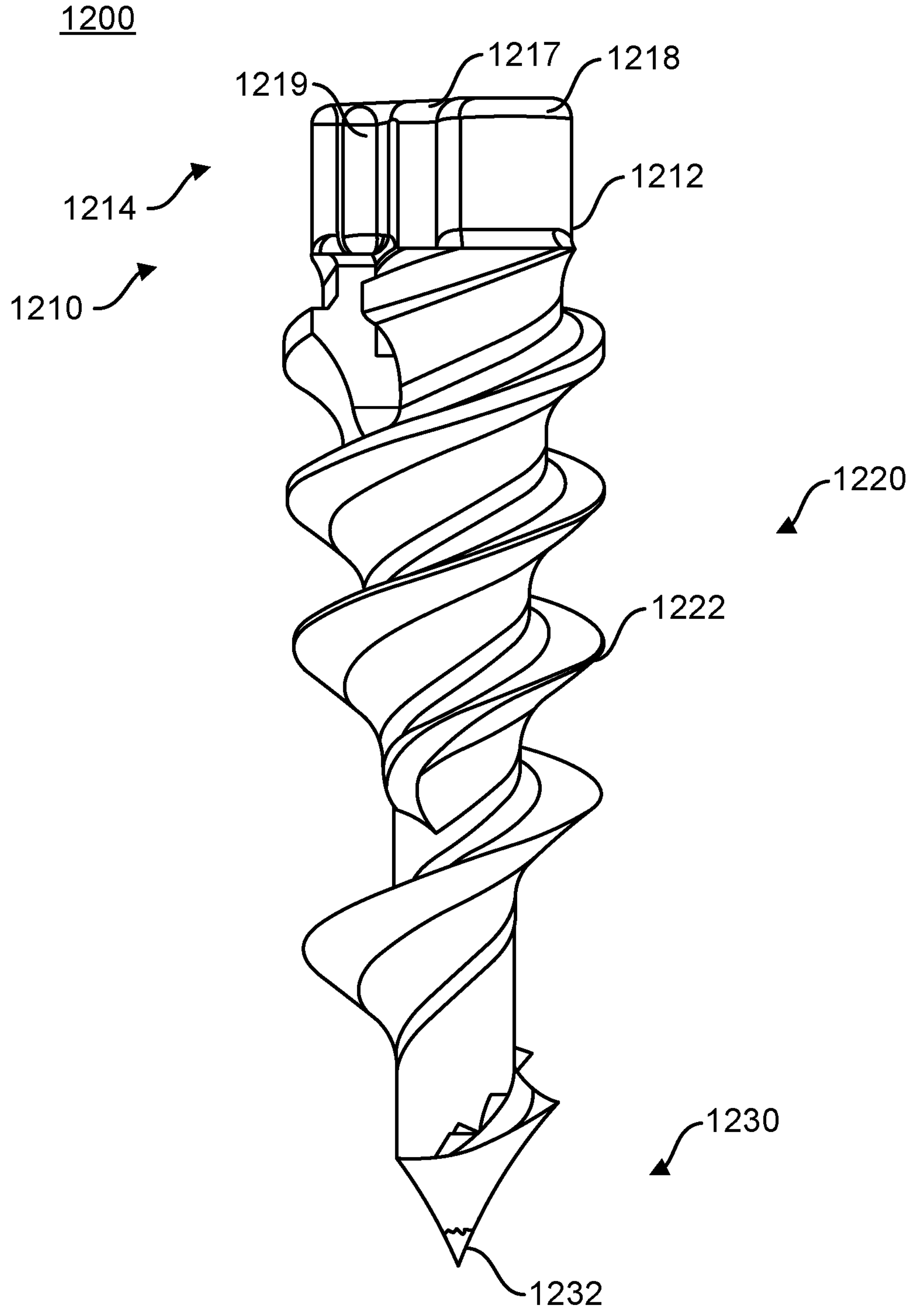
FIG. 25 is a rear left perspective view of the exemplary implant of FIG. 22 for facilitating soft tissue repair and/or reconstruction in conjunction with an implant system, in accordance with the present disclosure.
Figure 26:
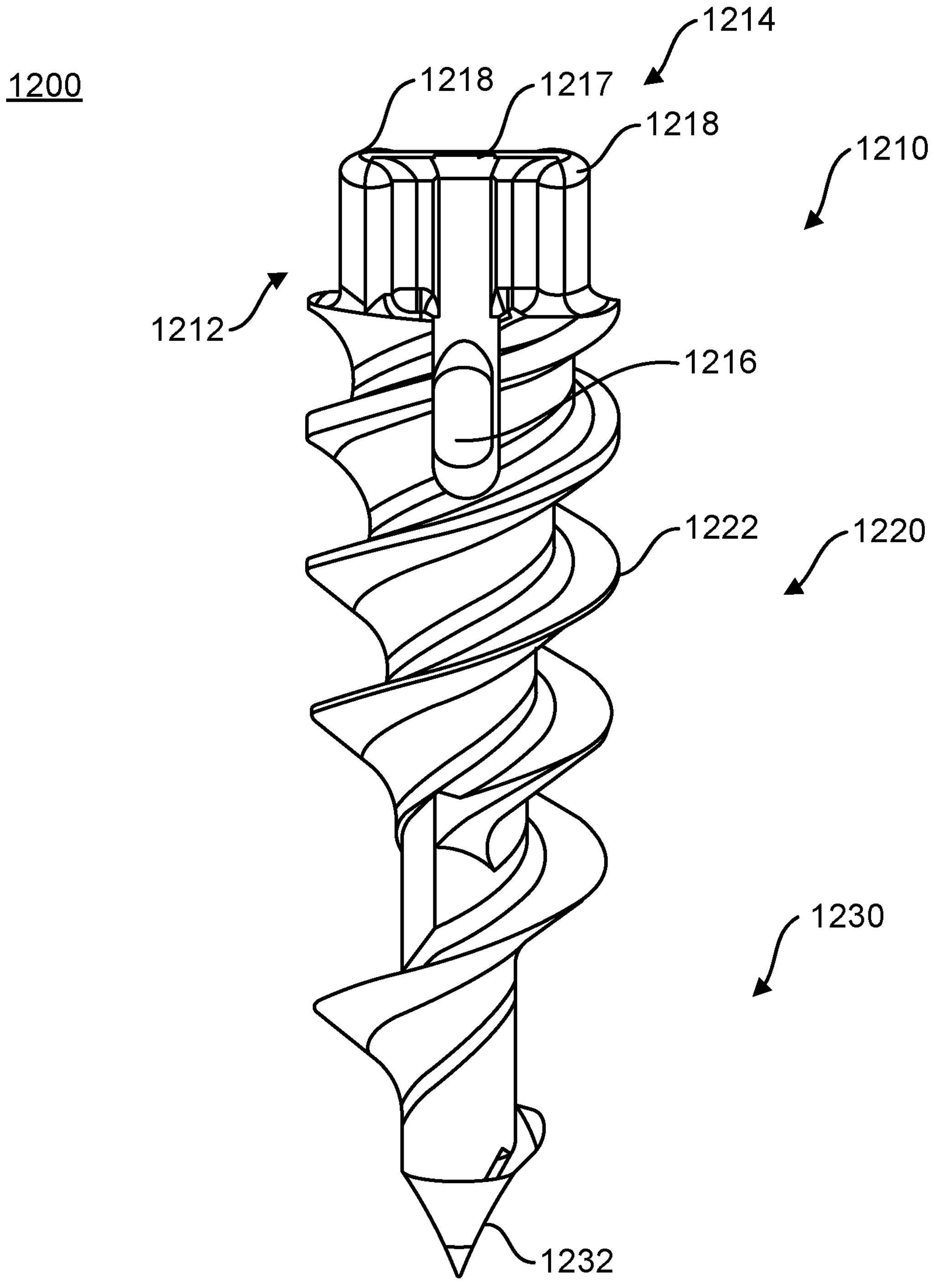
FIG. 26 is a front view of the exemplary implant of FIG. 22 for facilitating soft tissue repair and/or reconstruction in conjunction with an implant system, in accordance with the present disclosure.
Figure 27:
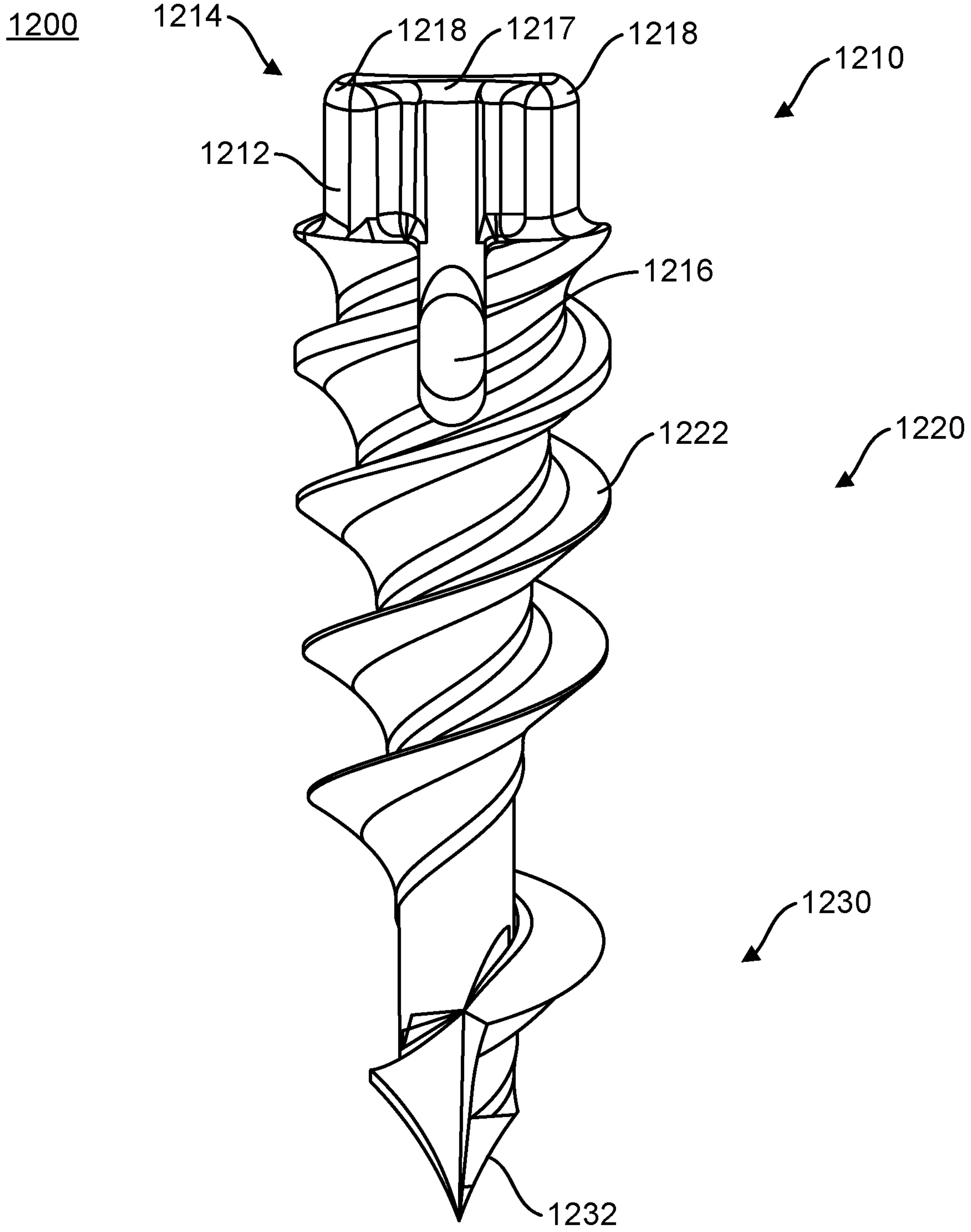
FIG. 27 is a rear view of the exemplary implant of FIG. 22 for facilitating soft tissue repair and/or reconstruction in conjunction with an implant system, in accordance with the present disclosure.
Figure 28:
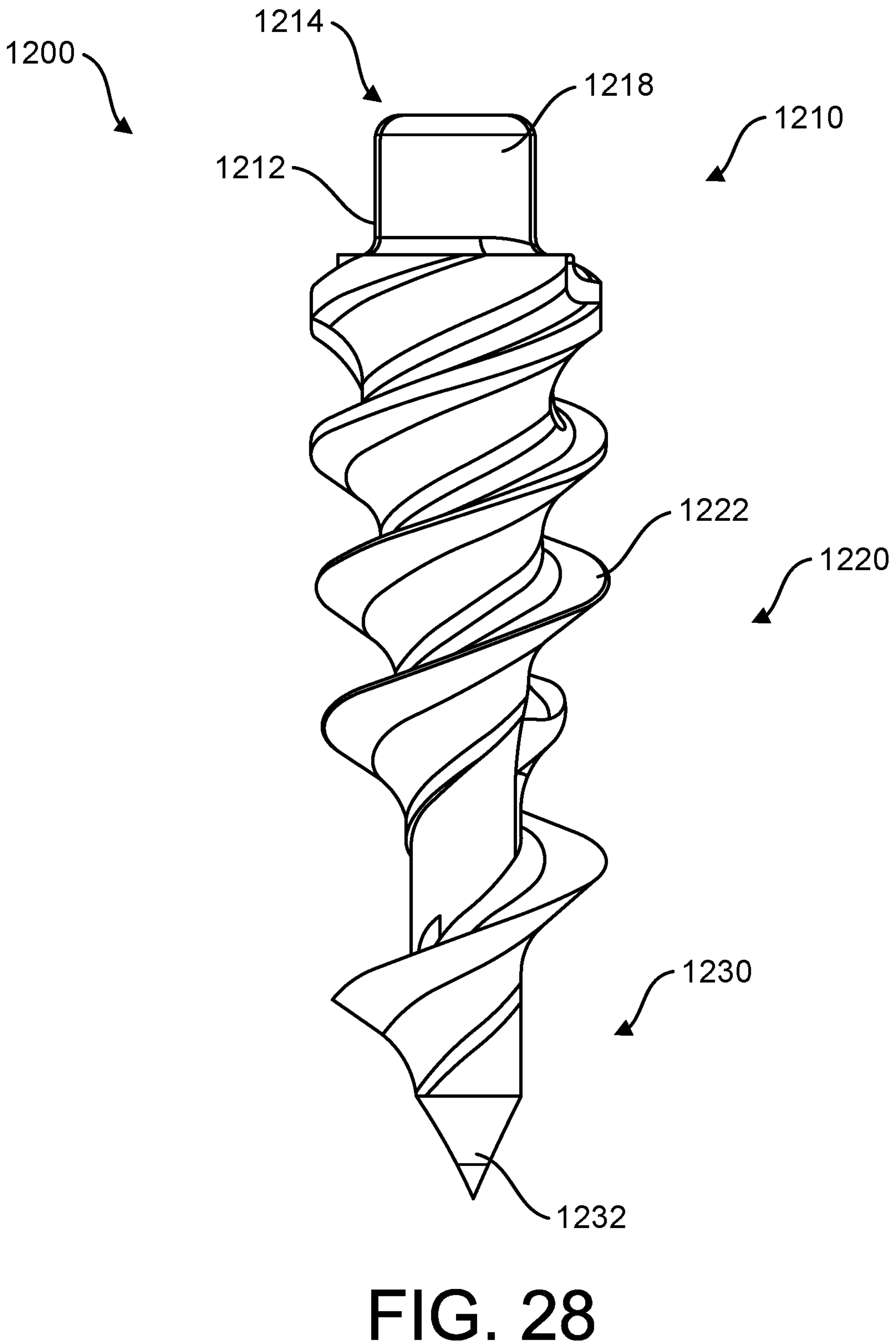
FIG. 28 is a side view of the exemplary implant of FIG. 22 for facilitating soft tissue repair and/or reconstruction in conjunction with an implant system, in accordance with the present disclosure.
Figure 29:
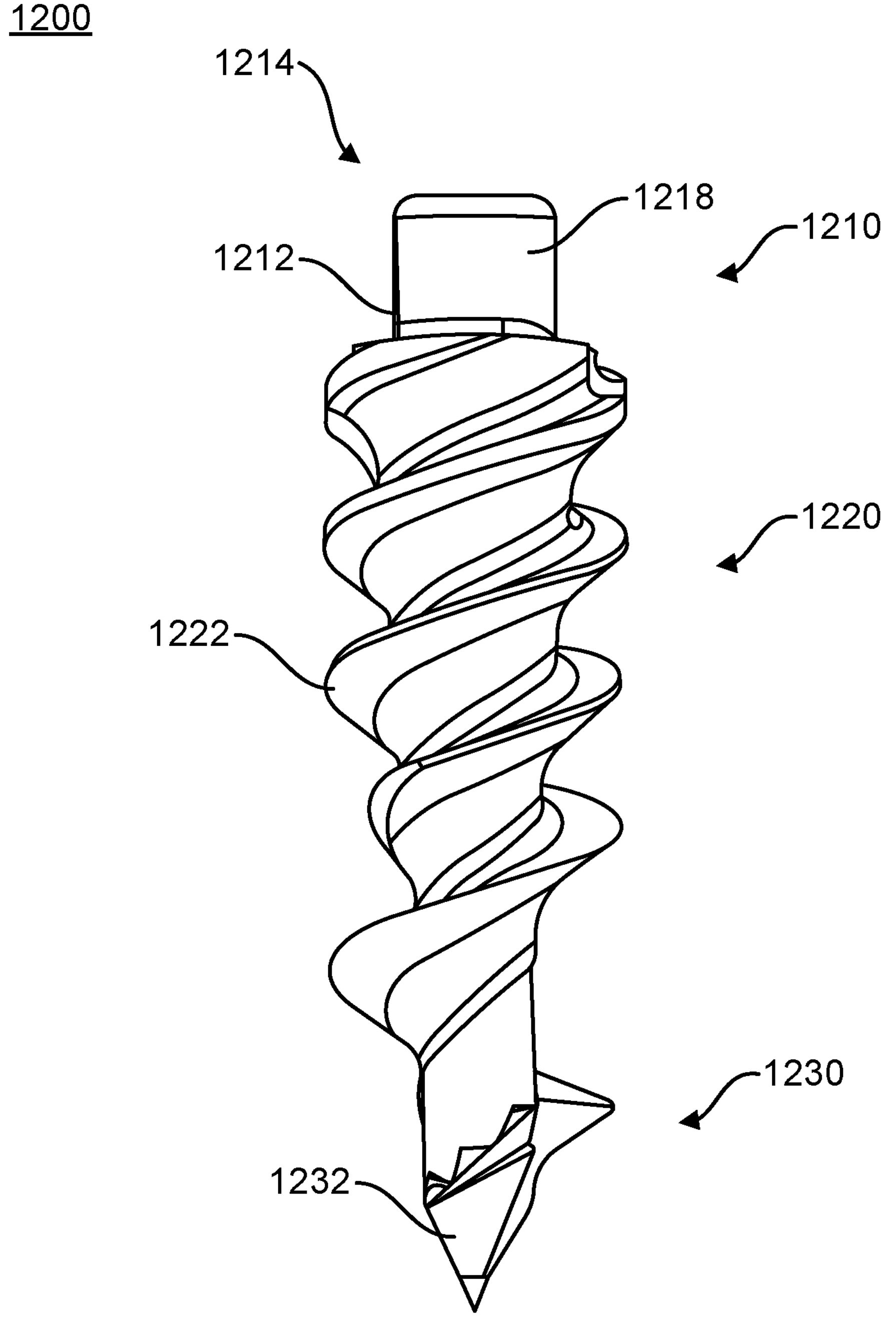
FIG. 29 is an opposite side view of the exemplary implant of FIG. 22 for facilitating soft tissue repair and/or reconstruction in conjunction with an implant system, in accordance with the present disclosure.
Figure 30:
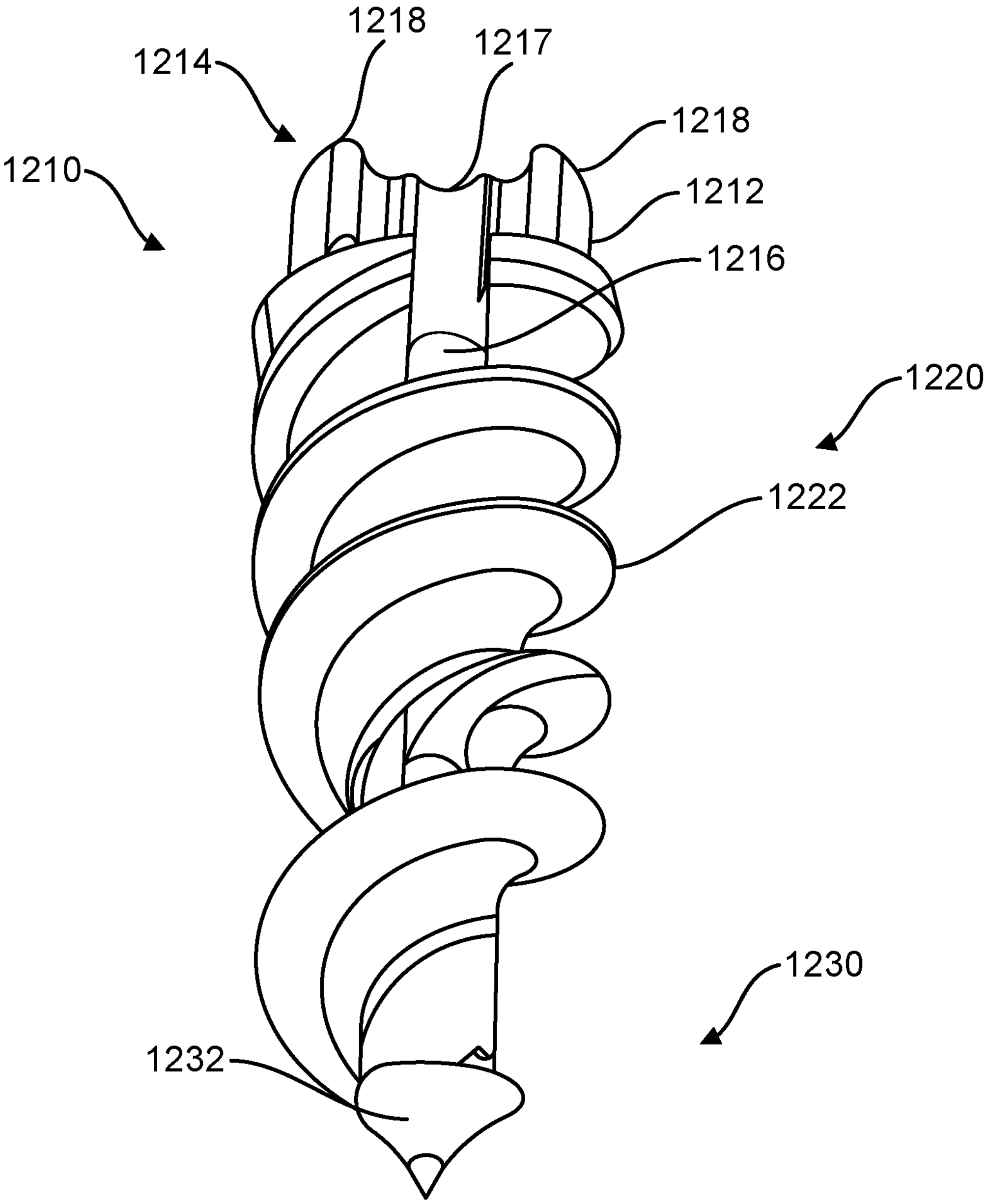
FIG. 30 is a front bottom perspective view of the exemplary implant of FIG. 22 for facilitating soft tissue repair and/or reconstruction in conjunction with an implant system, in accordance with the present disclosure.
Figure 31:
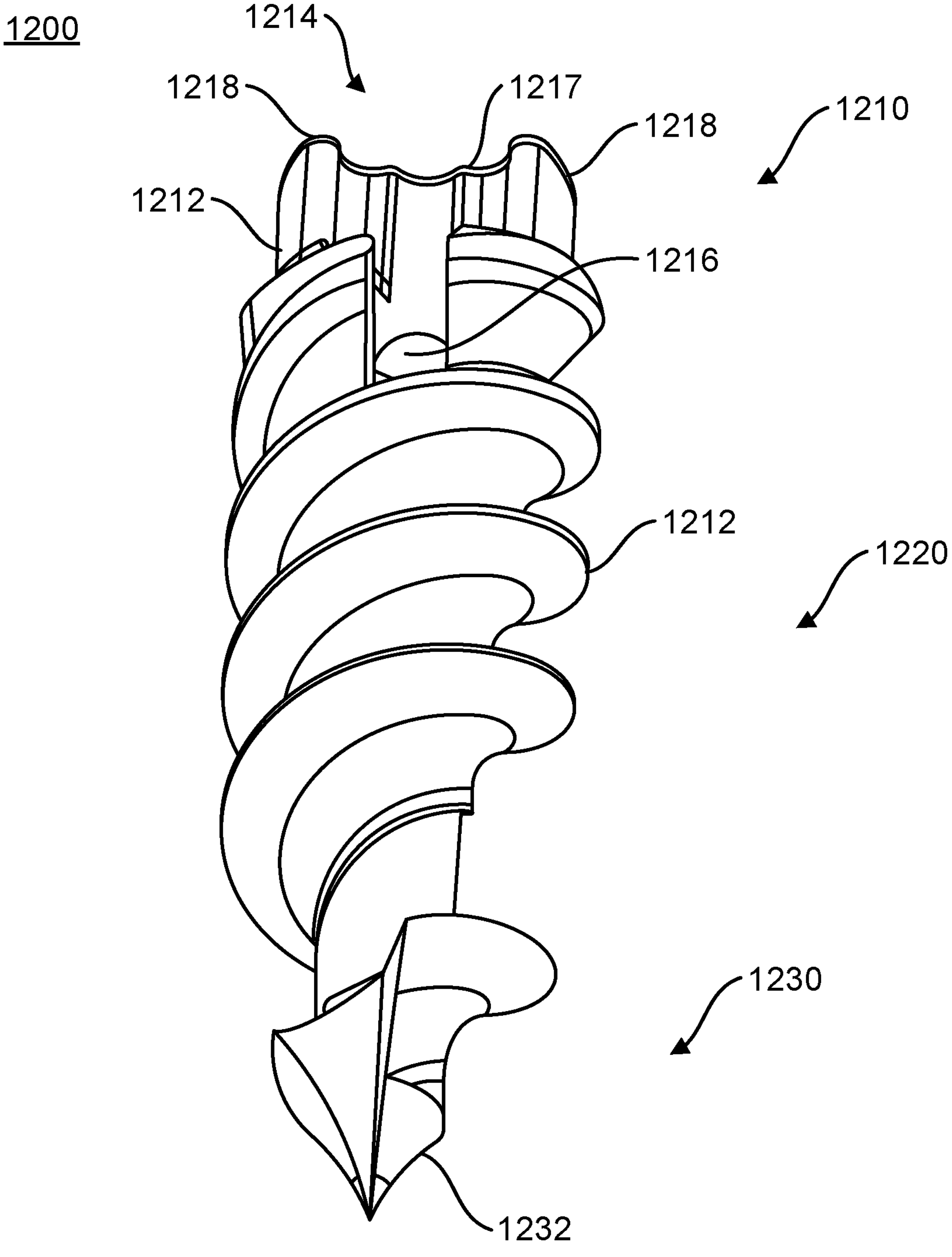
FIG. 31 is a rear bottom perspective view of the exemplary implant of FIG. 22 for facilitating soft tissue repair and/or reconstruction in conjunction with an implant system, in accordance with the present disclosure.
Figure 32:
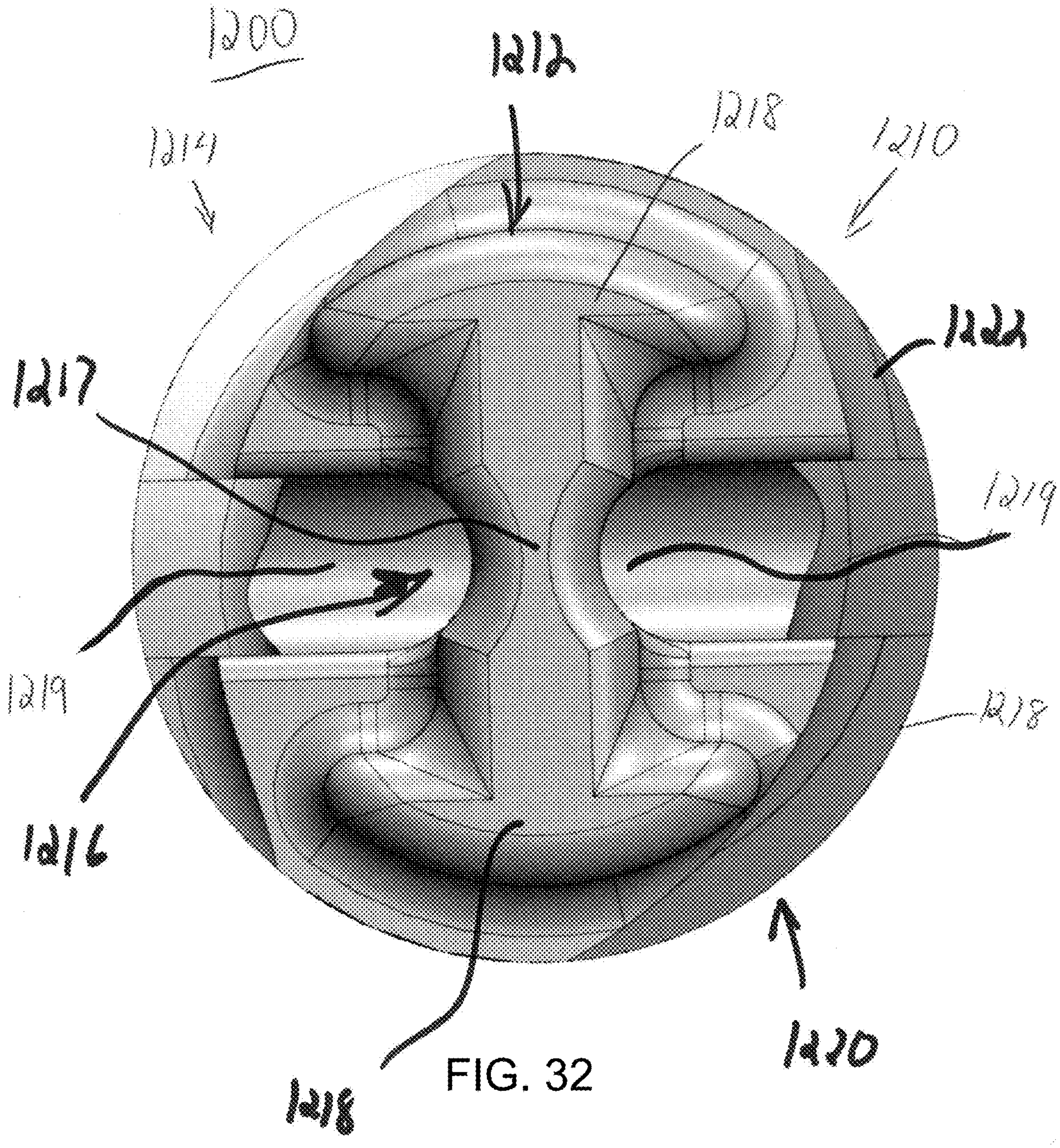
FIG. 32 is a top view of the exemplary implant of FIG. 22 for facilitating soft tissue repair and/or reconstruction in conjunction with an implant system, in accordance with the present disclosure.
Figure 33:
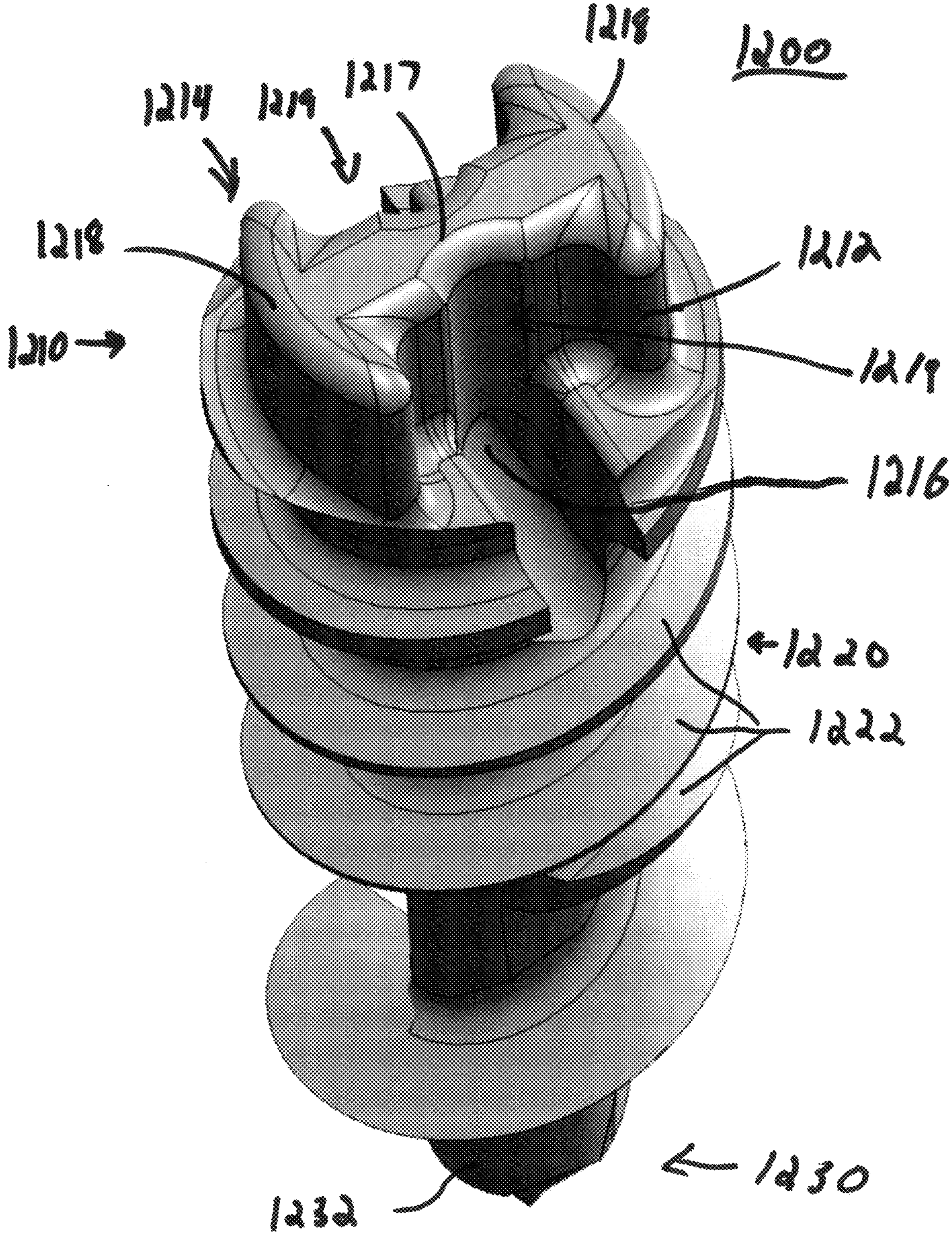
FIG. 33 is a front left top perspective view of the exemplary implant of FIG. 22 for facilitating soft tissue repair and/or reconstruction in conjunction with an implant system, in accordance with the present disclosure.
Figure 34:
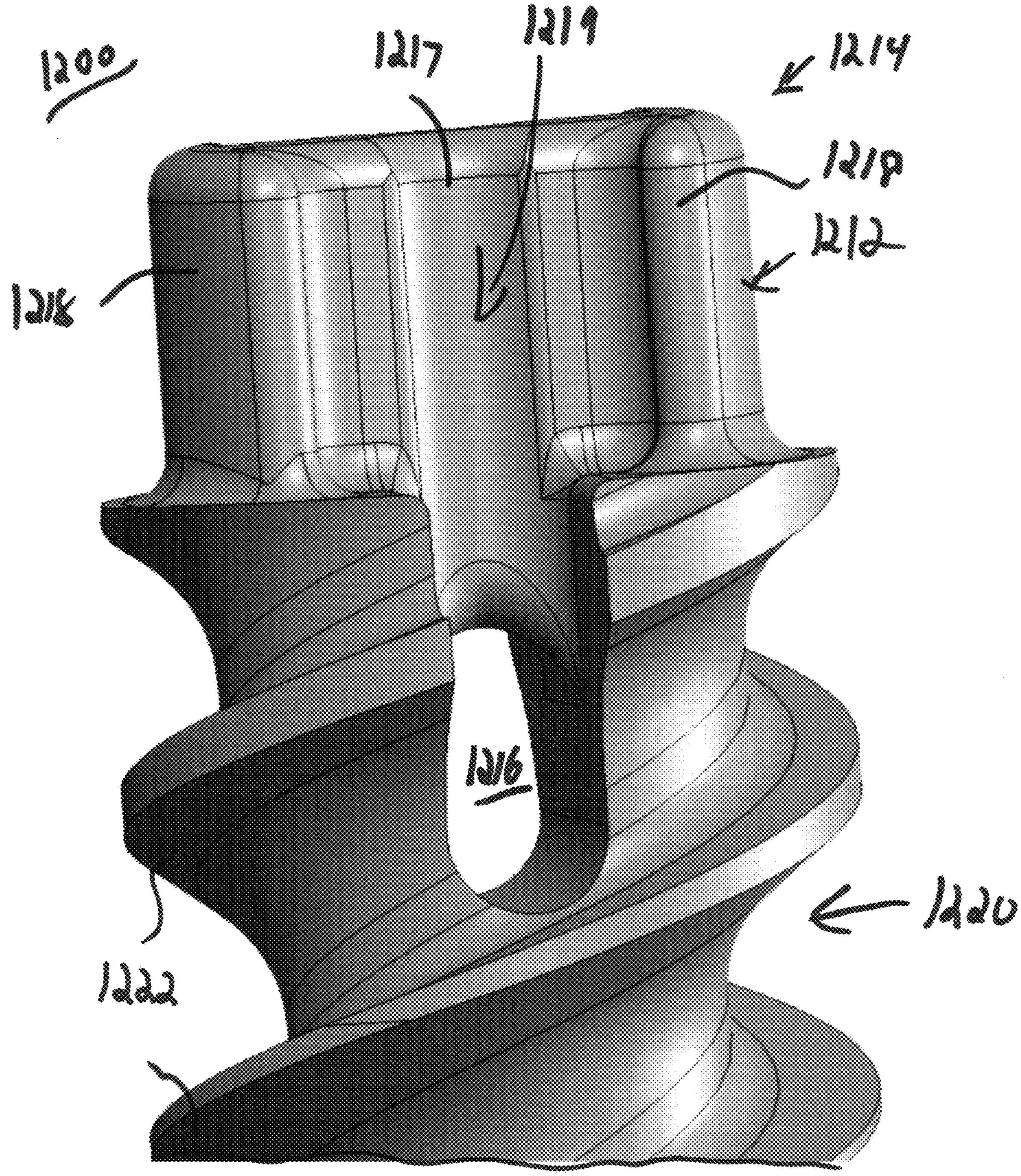
FIG. 34 is a front left elevational perspective view of the exemplary implant of FIG. 22 for facilitating soft tissue repair and/or reconstruction in conjunction with an implant system, in accordance with the present disclosure.
Figure 35:
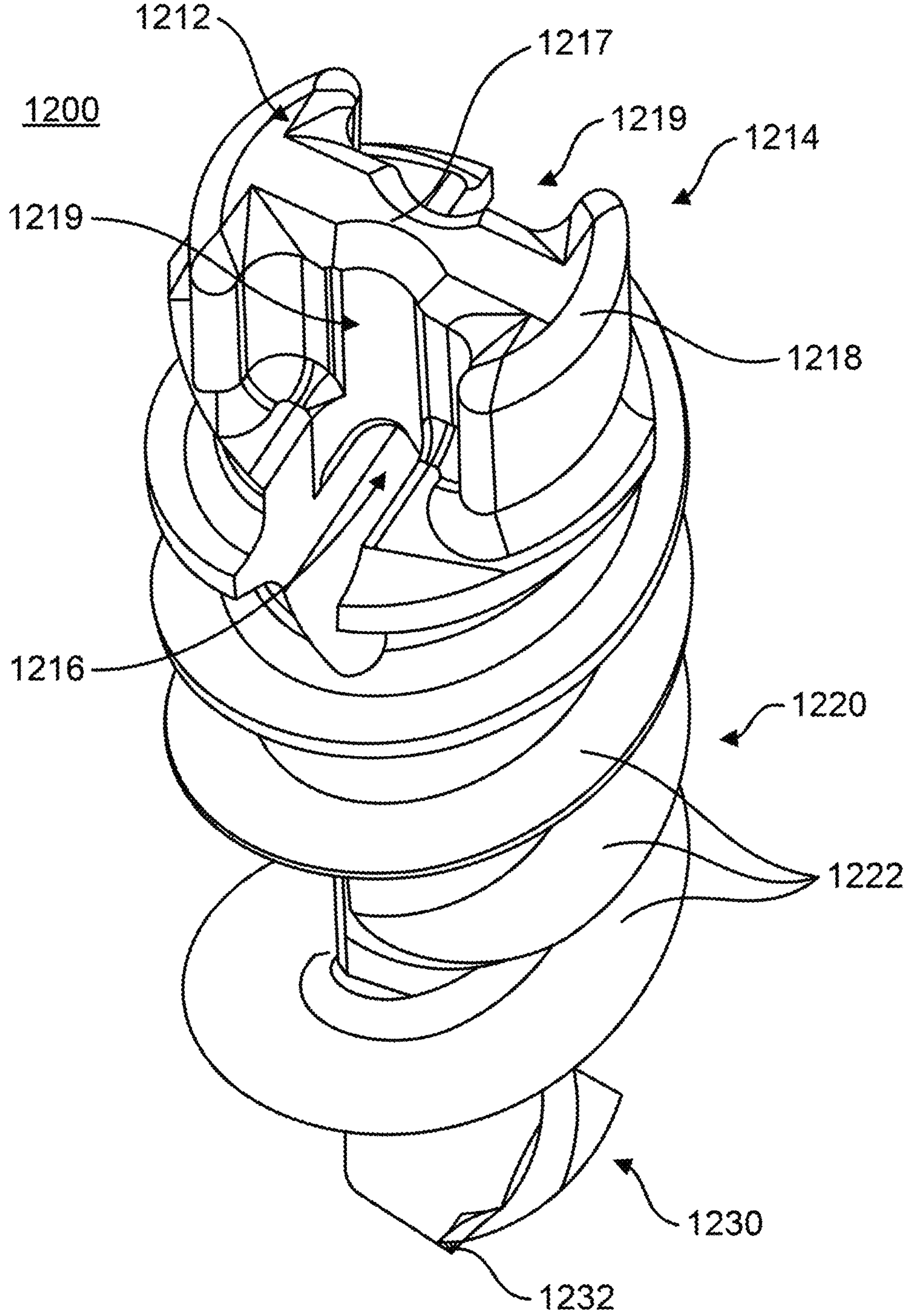
FIG. 35 is a top front right perspective view of the exemplary implant of FIG. 22 for facilitating soft tissue repair and/or reconstruction in conjunction with an implant system, in accordance with the present disclosure.
Figure 36:
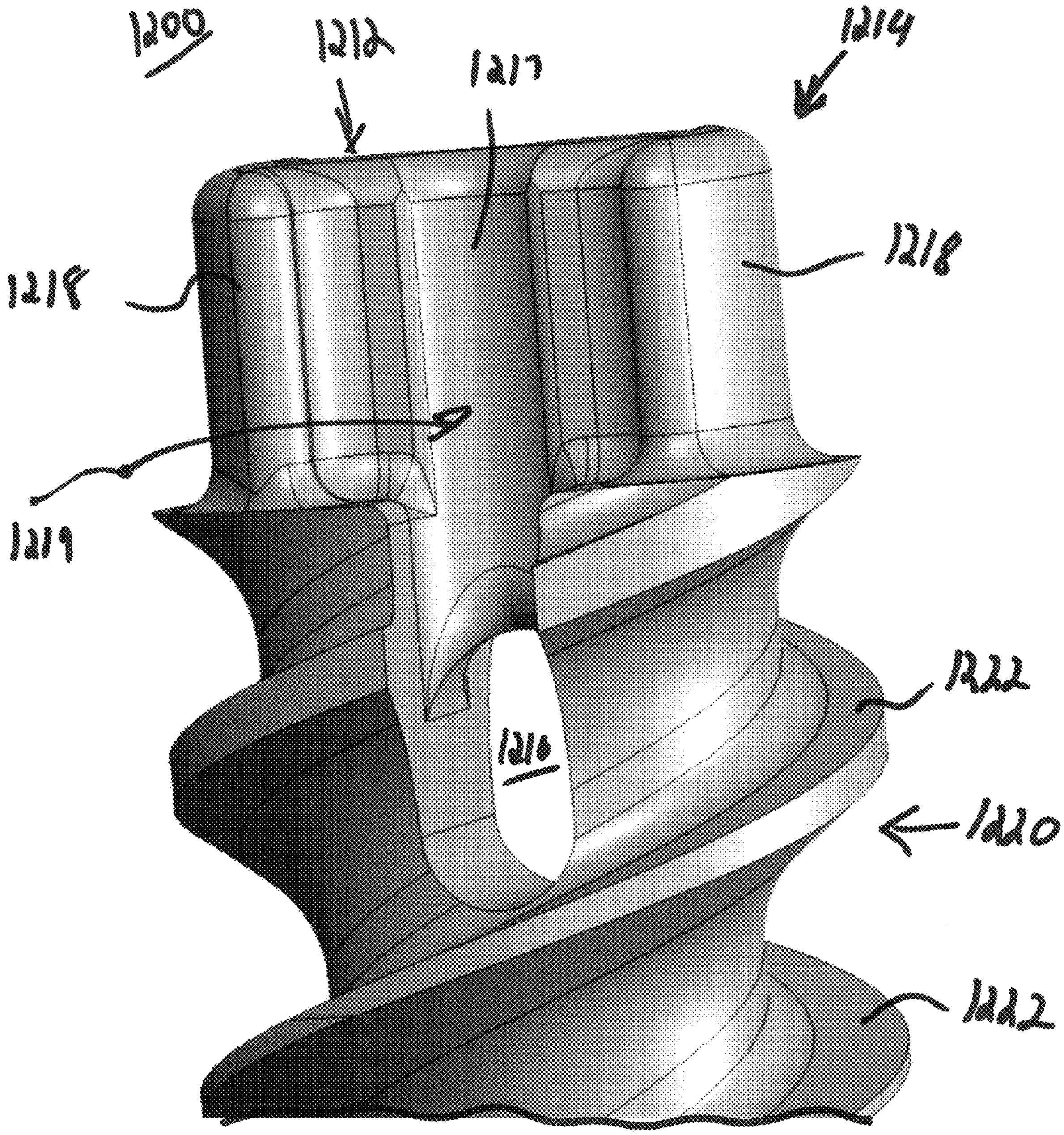
FIG. 36 is a front right elevational perspective view of the exemplary implant of FIG. 22 for facilitating soft tissue repair and/or reconstruction in conjunction with an implant system, in accordance with the present disclosure.
Figure 37:
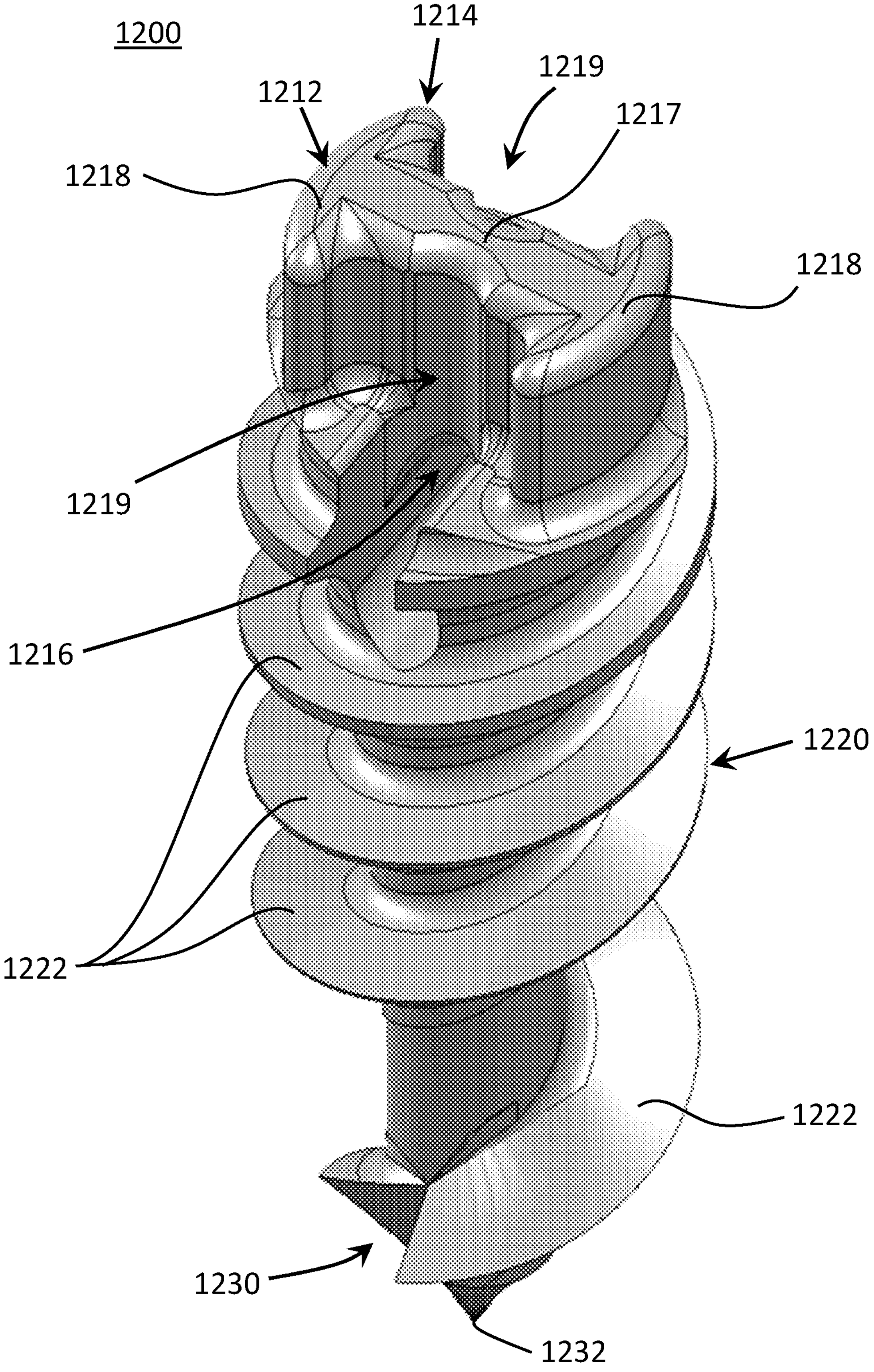
FIG. 37 is a rear left top perspective view of the exemplary implant of FIG. 22 for facilitating soft tissue repair and/or reconstruction in conjunction with an implant system, in accordance with the present disclosure.
Figure 38:
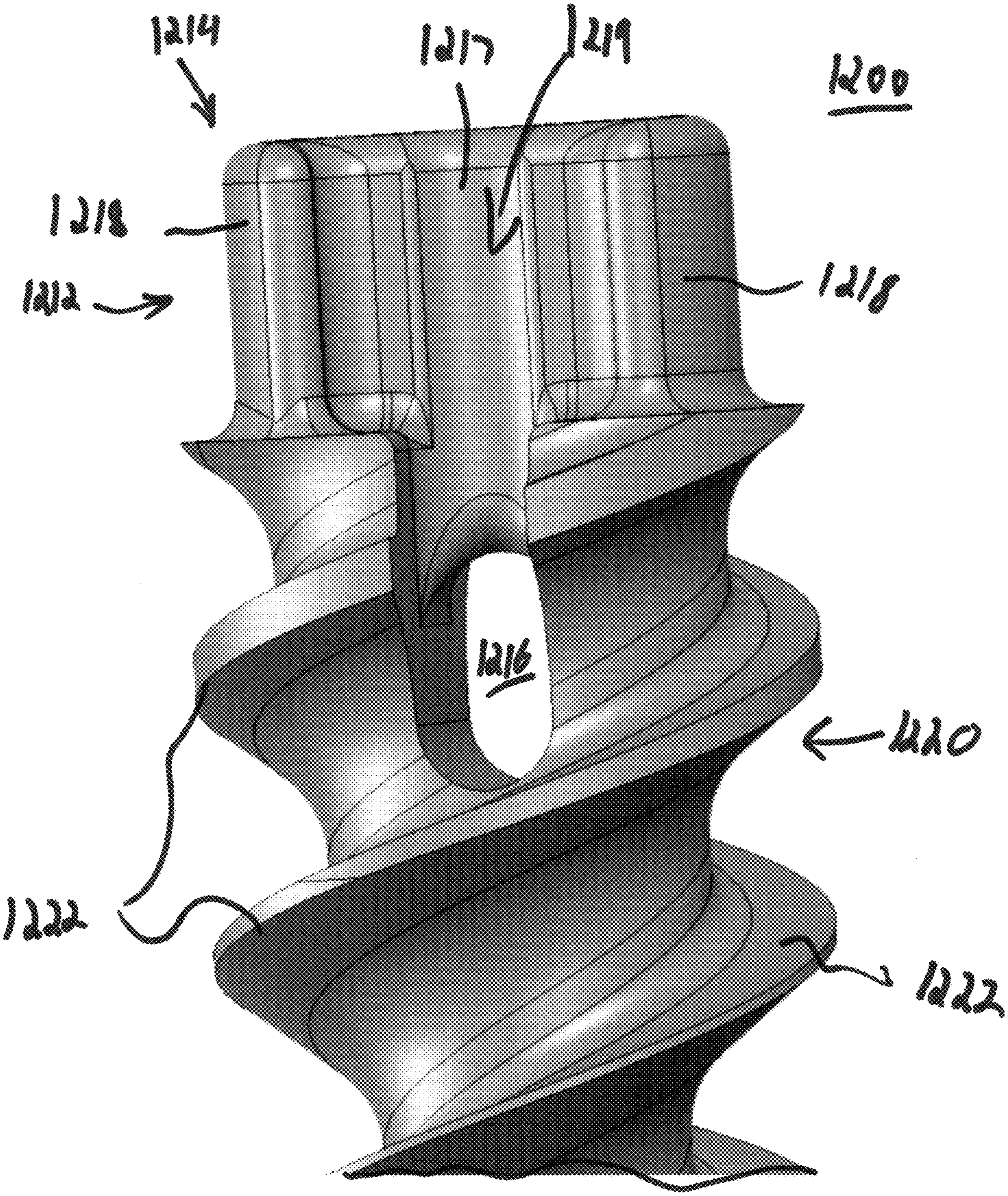
FIG. 38 is a rear left elevational perspective view of the exemplary implant of FIG. 22 for facilitating soft tissue repair and/or reconstruction in conjunction with an implant system, in accordance with the present disclosure.
Figure 39:
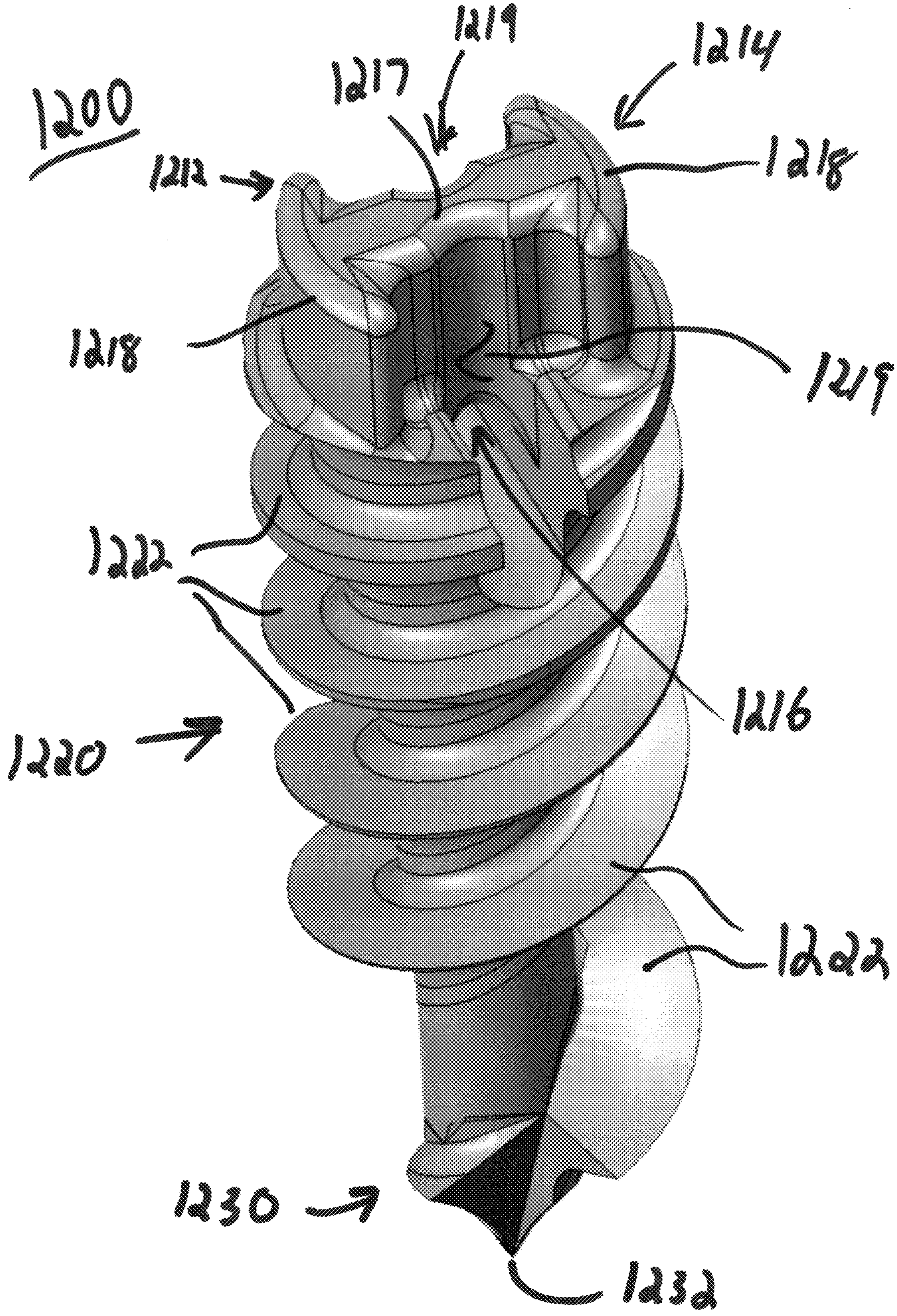
FIG. 39 is a rear right top perspective view of the exemplary implant of FIG. 22 for facilitating soft tissue repair and/or reconstruction in conjunction with an implant system, in accordance with the present disclosure.
Figure 40:
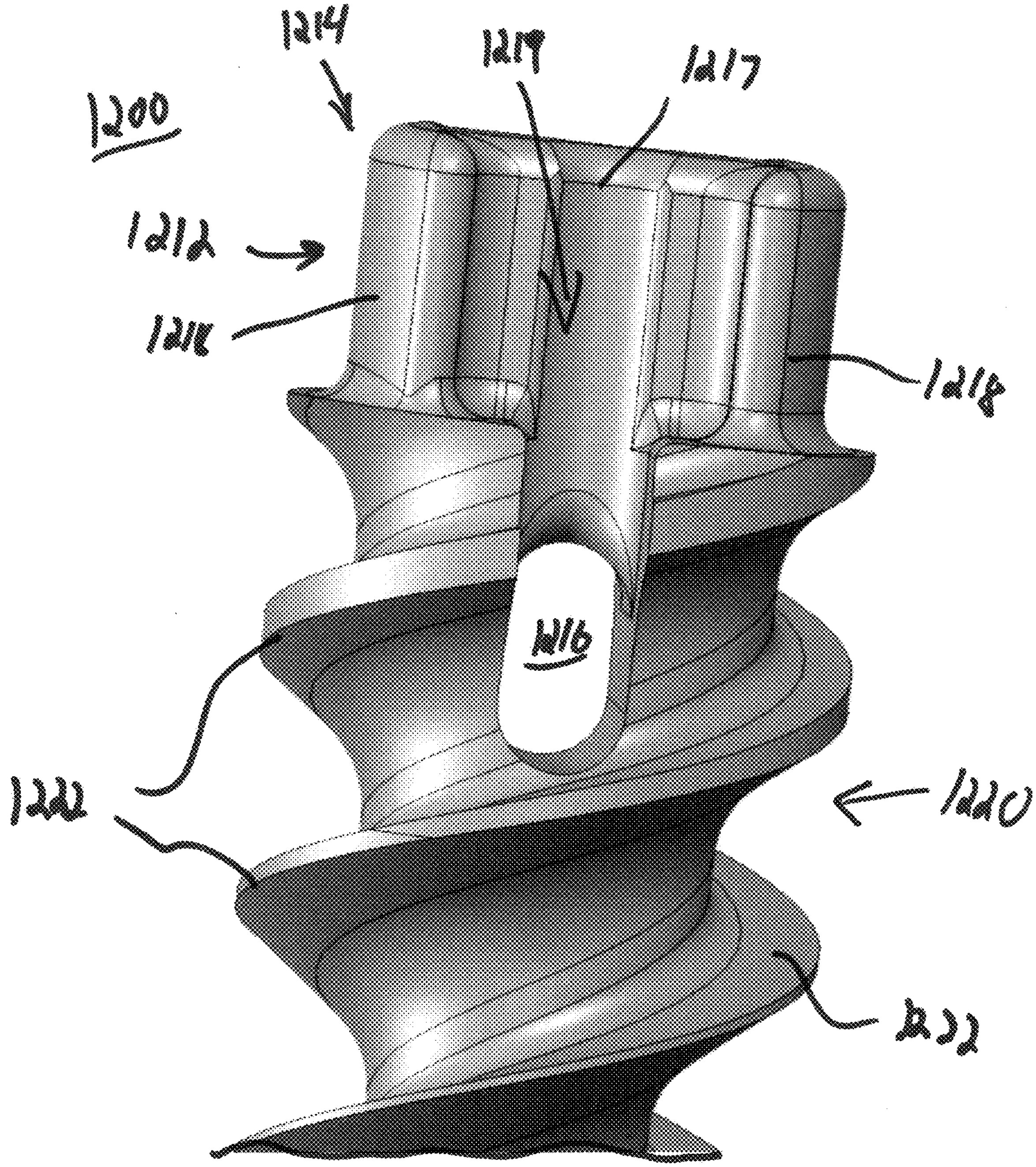
FIG. 40 is a rear right elevational perspective view of the exemplary implant of FIG. 22 for facilitating soft tissue repair and/or reconstruction in conjunction with an implant system, in accordance with the present disclosure.
Figure 41:
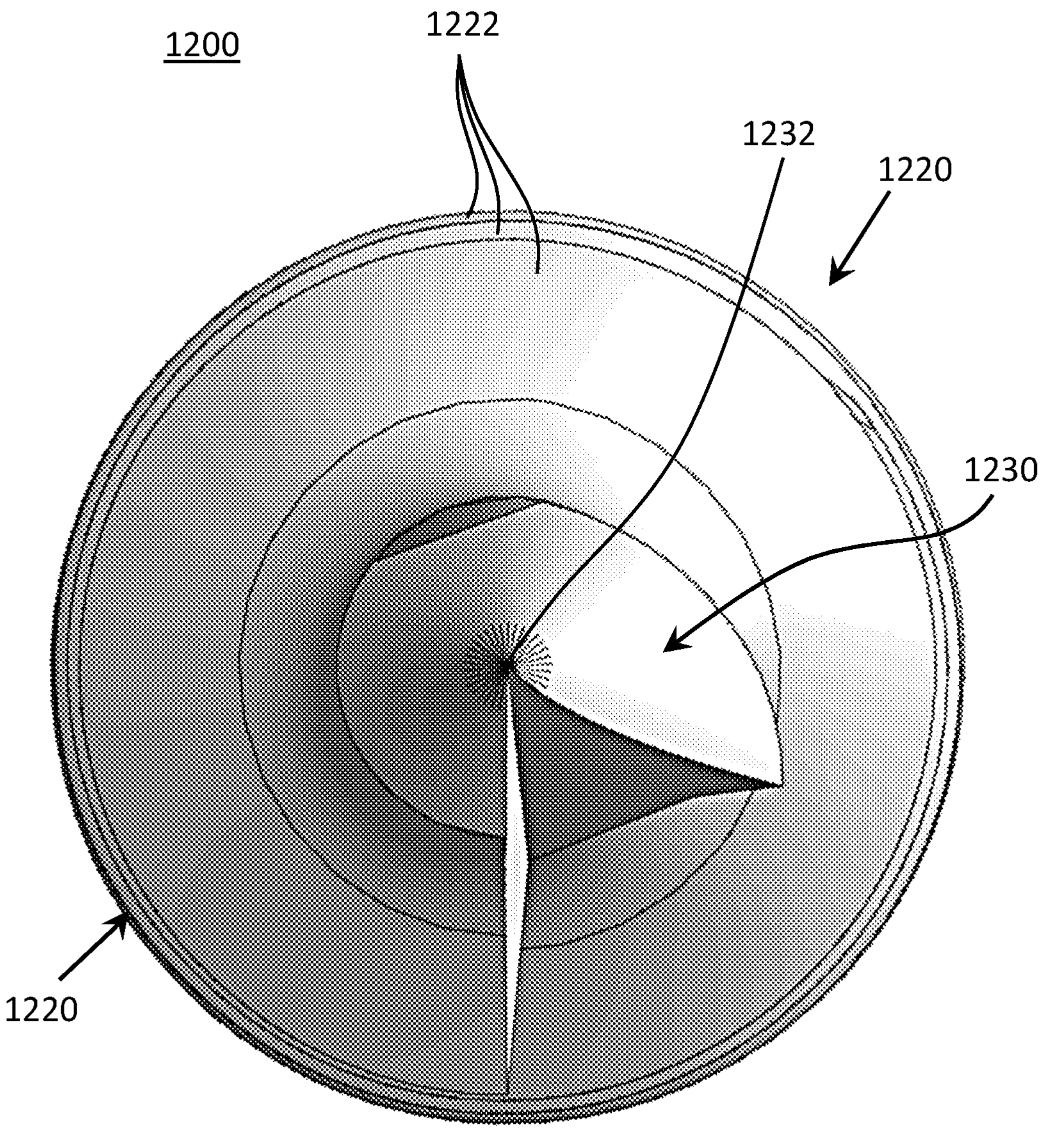
FIG. 41 is a bottom view of the exemplary implant of FIG. 22 for facilitating soft tissue repair and/or reconstruction in conjunction with an implant system, in accordance with the present disclosure.
Figure 42:
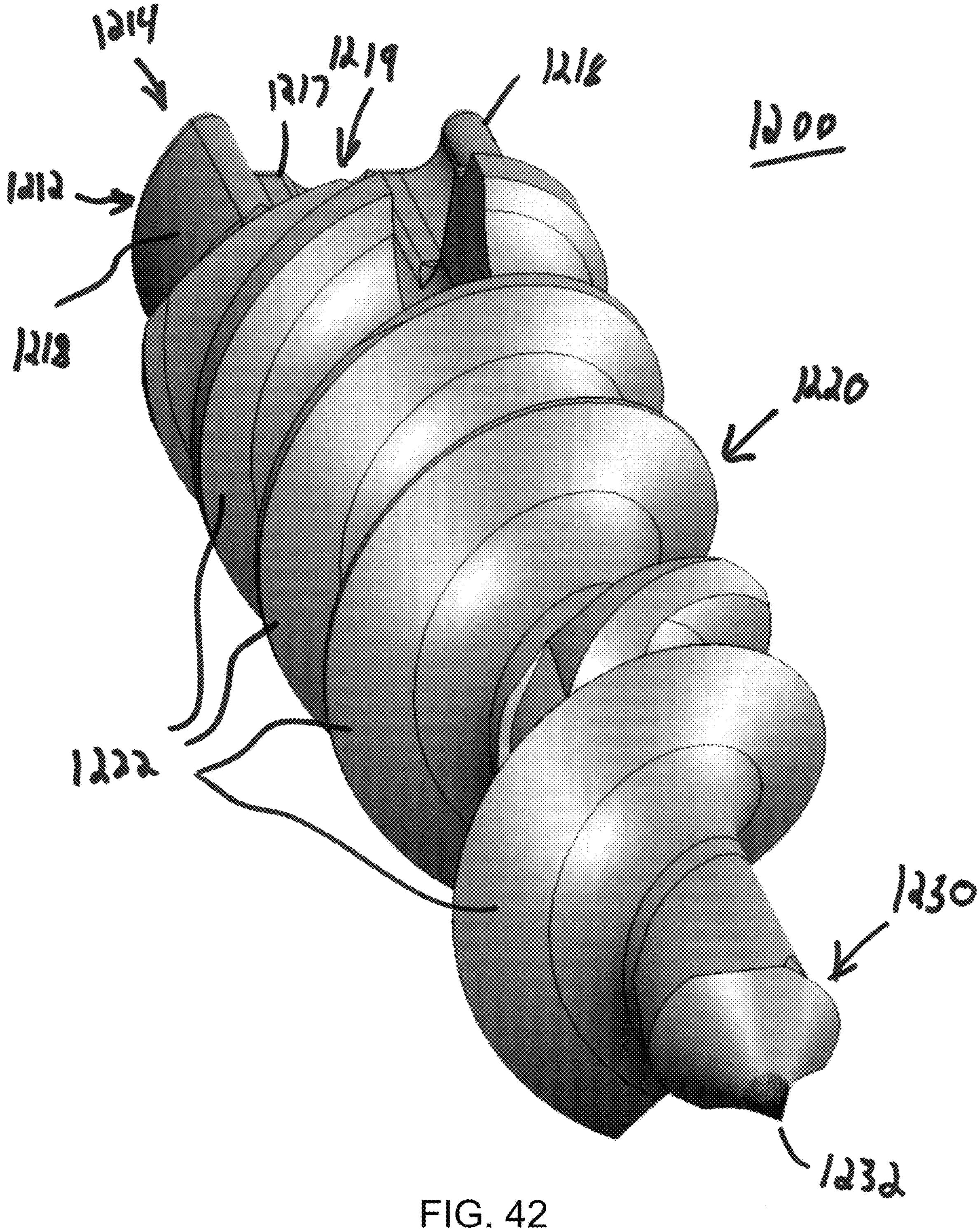
FIG. 42 is a front left bottom perspective view of the exemplary implant of FIG. 22 for facilitating soft tissue repair and/or reconstruction in conjunction with an implant system, in accordance with the present disclosure.
Figure 43:
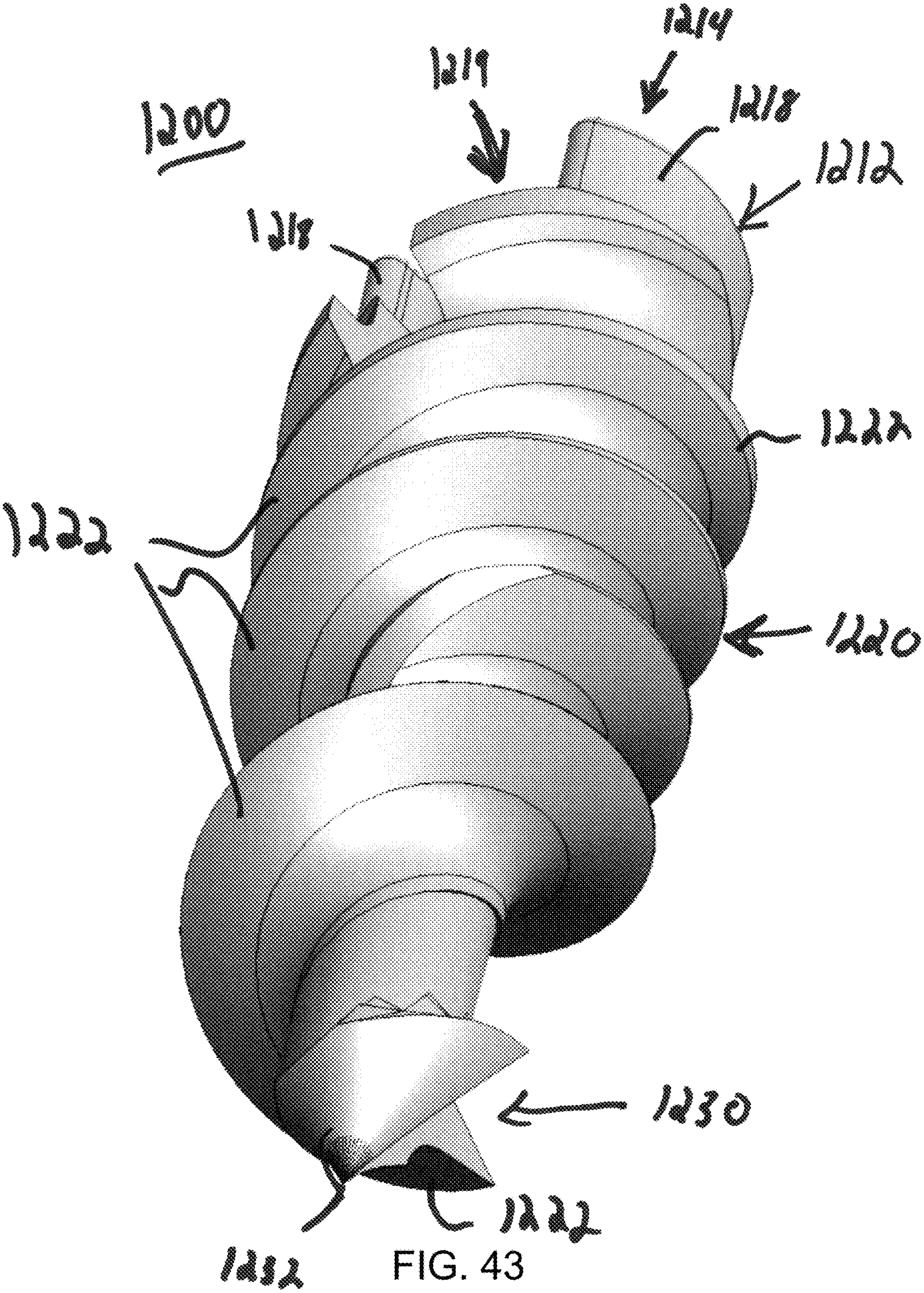
FIG. 43 is a front right bottom perspective view of the exemplary implant of FIG. 22 for facilitating soft tissue repair and/or reconstruction in conjunction with an implant system, in accordance with the present disclosure.
Figure 44:
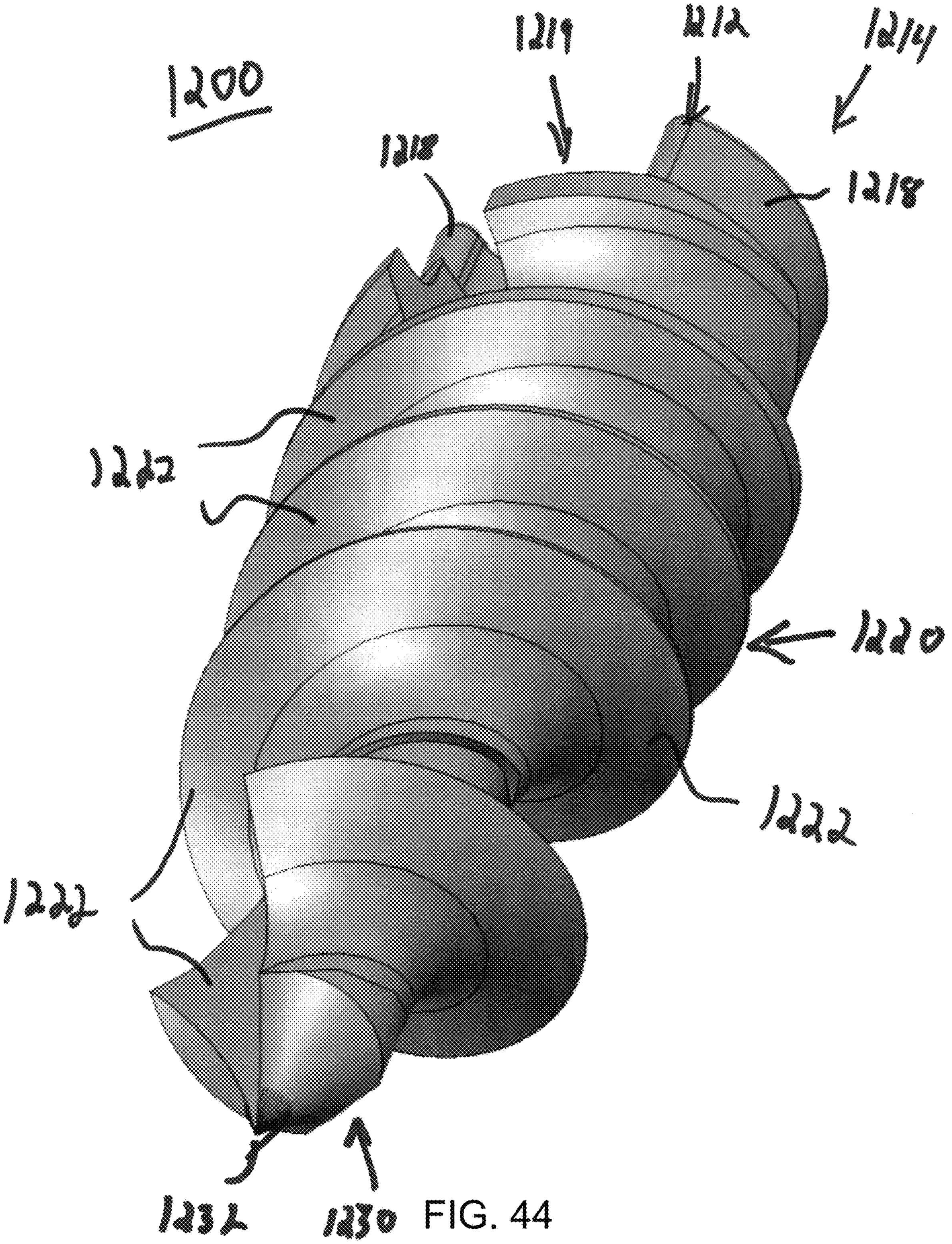
FIG. 44 is a rear left bottom perspective view of the exemplary implant of FIG. 22 for facilitating soft tissue repair and/or reconstruction in conjunction with an implant system, in accordance with the present disclosure.
Figure 45:
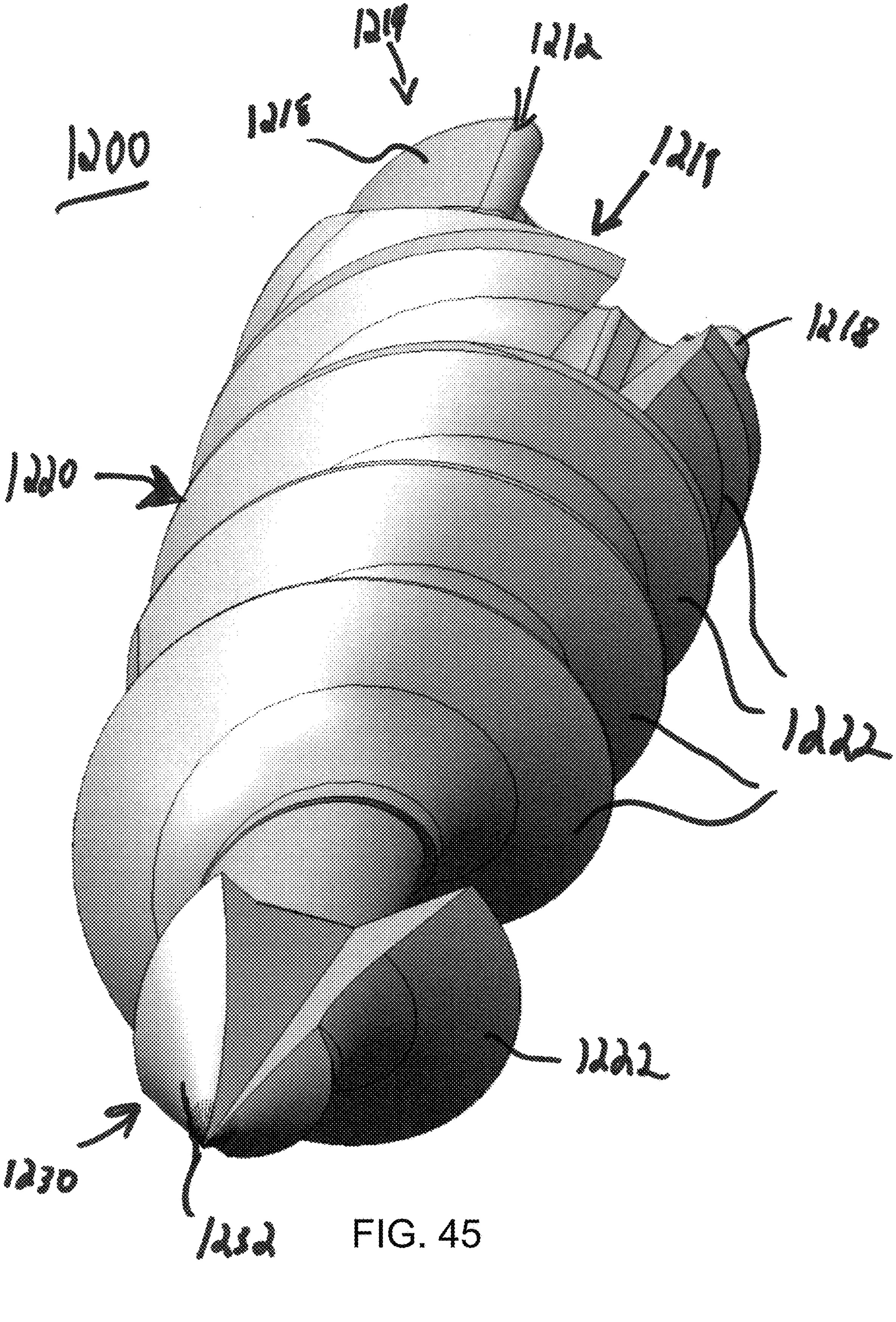
FIG. 45 is a rear right bottom perspective view of the exemplary implant of FIG. 22 for facilitating soft tissue repair and/or reconstruction in conjunction with an implant system, in accordance with the present disclosure.

The body portion 1220 of the implant 1200 is shown to include a threading 1222 arranged along a length of the body portion 1220. In some embodiments, the threading 1222 may extend proximally along the body portion 120 such that the threading 1222 terminates adjacent and/or abuts the interface feature 1214 of the top portion 1210. Further, the threading 1222 may further extend distally such that the threading 1222 terminates at a distal portion of the bottom portion 1230 of the implant 1200. The threading 1222 is shown to extend circumferentially around the implant 100 while extending continuously from the bottom portion 1230 to the top portion 1210. As shown in the exemplary embodiment of FIGS. 20-46, the threading 1222 is a dual-lead thread while in alternate embodiments, the threading 1222 may be a single-lead threading. In some embodiments, the threading 1222 may include alternate configurations and/or lengths. The threading 1222 is shown to include substantially equivalent spacing (e.g., distance between the threads in the proximal-distal direction when viewed as shown in FIG. 22) along the body portion 1220 of the implant 1200, with the threading 1222 having a greater spacing on the bottom portion 1230 of the implant 1200. In some embodiments, the threading 1222 may have equivalent spacing along the length of the implant 1200, whereas in other embodiments the threading 1222 may have one or more different spacing intervals along the length of the implant 1200. The threading 1222 may terminate in a tip portion 1232 of the bottom portion 1230 as shown in the exemplary embodiment of FIGS. 20-46. The tip portion 1232 may be configured to facilitate implantation of the implant 1200 into bone and/or soft tissue. Further, as the implant 1200 is implanted in bone and/or soft tissue, soft tissue may be pulled in the direction in which the implant 1200 is being inserted (e.g., into the bone) so as to achieve the desired placement of soft tissue from a displaced position. Once the implant 1200 is implanted, the implant 1200 may be disengaged from any instrument implemented during the implantation procedure of the implant 1200 and the suture may be tied off and/or coupled with other adjacent implants, anatomy, or sutures.

The implant 1200 may have one or more standard lengths, with the length measured from the proximal-most point of the top portion 1210 to the distal-most portion of the bottom portion 1230. For example, the implant 1200 may have a length ranging from 2 mm to 6 mm, with various different sized produced and/or provided in a surgical kit in increments of 0.5 mm. Additionally, the embodiment of the implant 1200 shown in FIGS. 20-46 may be available in multiple lengths (e.g., as components of a surgical kit or independently) so as to accommodate different applications of implantation into bone and/or soft tissue to facilitate repair and/or reconstruction of the soft tissue. Further, the implant 1200 may have a standard diameter and/or may be available in various different diameters so as to accommodate different applications of implantation into bone and/or soft tissue to facilitate repair and/or reconstruction of the soft tissue. Such various diameters may be components of a surgical kit (e.g., a sterile kit including multiple lengths and diameters of the implant 1200 as well as other components, for example one or more k-wires, drills, and/or drivers) and/or may be available independently of such a kit. The implant 1200 may preferably be fabricated from titanium, although the implant 1200 may also be available in PEEK and/or other polymeric soft anchor configurations. In some aspects, the implant 1200 may be produced and/or provided with a suture (e.g., those shown and described in the patent applications referenced previously, or other similar sutures and/or suture tapes) threaded through the opening 1216. Further, in some aspects the implant 1200 may be produced and/or provided (e.g., in a sterile surgical kit) in a pre-loaded state, where the implant 1200 is engaged with an instrument 1250 via the interface feature 1214 and a suture as described previously threaded through the implant 1200 and at least a portion of the instrument 1250.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

In some computer aided drawing/renderings/figures of the application, tangent or wireframe lines (sometimes referred to as intersection lines, tangential edges or tessellation lines) are included by the respective software. Such lines are meant as contour lines, and are not actually part of the ornamental visual appearance (or design) (i.e., are not themselves ornamental features) of the respective implant, instruments, system, etc., but are merely included as a visual aid to allow better understanding of the contours of the design thereof.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A system for repairing or reconstructing soft tissue, the system comprising:

an instrument having a handle and an extension, the extension opposite the handle;

an implant releasably engaged with the instrument; and a suture threaded through at least a portion of the implant, wherein the suture is engaged with a tensioning mechanism of the instrument, wherein the implant comprises:

a head portion at a top end of the implant configured to releasably engage with the instrument; and an externally threaded body portion extending longitudinally from the head to a tip portion at a bottom end of the implant configured to facilitate implantation of the implant into bone and/or soft tissue, wherein the head portion comprises an interface feature with a pair of arc-shaped protrusions on substantially opposite lateral sides of the head portion that are separated and connected by a bridge portion extending laterally therebetween, wherein the pair of arc-shaped protrusions and the bridge portion form a pair of voids positioned on substantially opposite lateral sides of the head portion, and wherein the body portion comprises an opening extending laterally therethrough.

2. The system of claim 1, wherein the head portion further comprises a pair of longitudinal grooves on substantially opposite sides of the bridge portion.

3. The system of claim 2, wherein the pair of longitudinal grooves longitudinally extend to the opening.

4. The system of claim 1, wherein the pair of voids of the head portion of the implant are positioned on first and second lateral sides of the implant, and wherein the opening of the body portion of the implant extends laterally between the first and second lateral sides of the implant.

5. The system of claim 1, wherein the head portion, the bottom tip portion, and the body portion of the implant are arranged about a common longitudinal axis.

6. The system of claim 1, wherein the implant is monolithic.

7. The system of claim 1, wherein an external threading of the body portion is of a variable pitch as it extends from the head portion to the bottom tip portion.

8. The system of claim 1, wherein the implant further comprises:

at least one tap arranged on an outer surface of the bottom tip portion of the implant.

9. The system of claim 1, wherein the implant is releasably couplable with a tip of the extension of the instrument.

10. The system of claim 9, wherein the tip of the extension of the instrument comprises a cavity that is configured to releasably receive and couple with the interface feature of the implant.

11. The system of claim 9, wherein the instrument comprises the tensioning mechanism disposed within a housing of the instrument.

12. The system of claim 11, wherein the tensioning mechanism comprises:

a first arm;

a second arm; and a resilient member.

13. The system of claim 12, wherein the second arm is pivotably coupled with the first arm.

14. The system of claim 13, wherein the instrument further comprises:

a track disposed on at least a portion of an outer surface of the handle, wherein the track is configured to receive at least a portion of the suture at least partially therein.

15. The system of claim 14, wherein the second arm comprises an engagement portion configured to engage with at least a portion of the suture, wherein the engagement portion is arranged adjacent to at least a portion of the track.

16. The system of claim 15, wherein the resilient member is a spring.

17. The system of claim 16, wherein actuation of at least one of the first arm and the second arm compresses the spring.

18. An implant, comprising:

a head portion at a top end of the implant configured to releasably engage with the instrument; and an externally threaded body portion extending longitudinally from the head to a tip portion at a bottom end of the implant configured to facilitate implantation of the implant into bone and/or soft tissue, wherein the head portion comprises an interface feature with a pair of arc-shaped protrusions on substantially opposite lateral sides of the head portion that are separated and connected by a bridge portion extending laterally therebetween, wherein the pair of arc-shaped protrusions and the bridge portion form a pair of voids positioned on substantially opposite lateral sides of the head portion, wherein the body portion comprises an opening extending laterally therethrough, and wherein the head portion further comprises a pair of longitudinal grooves on substantially opposite sides of the bridge portion that extend longitudinally to the opening.

19. The implant of claim 18, wherein the pair of voids of the head portion of are positioned on first and second lateral sides of the implant, and wherein the opening of the body portion extends laterally between the first and second lateral sides.

20. The implant of claim 18, wherein the implant is monolithic, wherein an external threading of the body portion is of a variable pitch, and wherein the bottom tip portion comprises at least one tap feature arranged on an outer surface thereof.

* * * * *